(12) United States Patent
Li et al.

(10) Patent No.: US 7,629,344 B2
(45) Date of Patent: Dec. 8, 2009

(54) 3-(IMIDAZOLYL)-PYRAZOLO[3,4-B] PYRIDINES

(75) Inventors: Lianfa Li, Palo Alto, CA (US); Andrew M. K. Pennell, San Francisco, CA (US); Penglie Zhang, Foster City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 12/124,894

(22) Filed: May 21, 2008

(65) Prior Publication Data

US 2008/0300257 A1    Dec. 4, 2008

Related U.S. Application Data

(60) Provisional application No. 60/932,948, filed on May 22, 2007.

(51) Int. Cl.
C07D 487/04 (2006.01)
A61K 31/437 (2006.01)

(52) U.S. Cl. .................. 514/253.04; 544/362
(58) Field of Classification Search ............ None
See application file for complete search history.

(56) References Cited

U.S. PATENT DOCUMENTS

| 4,238,497 A | 12/1980 | Black et al. |
| 4,443,466 A | 4/1984 | Karjalainen et al. |
| 4,927,942 A | 5/1990 | Speranza et al. |
| 7,157,464 B2 | 1/2007 | Pennell et al. |
| 7,449,576 B1 | 11/2008 | Pennell et al. |
| 2004/0082571 A1 | 4/2004 | Pennell et al. |
| 2004/0162282 A1 | 8/2004 | Pennell et al. |
| 2005/0234034 A1 | 10/2005 | Pennell et al. |
| 2005/0256130 A1 | 11/2005 | Pennell et al. |
| 2006/0074121 A1 | 4/2006 | Chen et al. |
| 2006/0106218 A1 | 5/2006 | Pennell et al. |
| 2007/0010523 A1 | 1/2007 | Zhang et al. |
| 2007/0010524 A1 | 1/2007 | Zhang et al. |
| 2008/0058341 A1* | 3/2008 | Zhang et al. ........... 514/252.16 |

FOREIGN PATENT DOCUMENTS

| WO | WO 03/105853 A1 | 12/2003 |
| WO | WO 2005/056015 A1 | 6/2005 |
| WO | WO 2005/084667 A1 | 9/2005 |
| WO | WO 2007/027734 A2 | 3/2007 |
| WO | WO 2007/027734 A3 | 3/2007 |

OTHER PUBLICATIONS

Melter et al. Current Opinion in Organ Transplantation, vol. 7, p. 77-84 (2002).*
Gladue et al. Chemokine Biology, vol. II, p. 103-113 (2007).*
Bendele, A. et al., "Animal Models of Arthritis: Relevance to Human Disease," *Toxicologic Pathology*, 1999, vol. 27, No. 1, pp. 134-142.
Bendele, A. et al., "Efficacy of Sustained Blood Levels of Interleukin-1 Receptor Antagonist in Animal Models of Arthritis," *Arthritis & Rheumatism*, Mar. 1999, vol. 42, No. 3, pp. 498-506.
Dairaghi, D.J. et al., "Chemokine Receptor CCR3 Function Is Highly Dependent on Local pH and Ionic Strength," *The Journal of Biological Chemistry*, Nov. 7, 1997, vol. 272, No. 45, pp. 28206-28209.
Dairaghi, D.J. et al., "HHV8-encoded vMIP-I Selectively Engages Chemokine Receptor CCR8," *The Journal of Biological Chemistry*, Jul. 30, 1999, vol. 274, No. 31, pp. 21569-21574.
Hesselgesser, J. et al., "Identification and Characterization of Small Molecule Functional Antagonists of the CCR1 Chemokine Receptor," *The Journal of Biological Chemistry*, Jun. 19, 1998, vol. 273, No. 25, pp. 15687-15692.
International Search Report mailed on Aug. 6, 2008, for International Application No. PCT/US08/64374 filed on May 21, 2008, 2 pages.
Jones, J. et al., "British Society of Gastroenterology guidelines for the management of the irritable bowel syndrome," Division of Gastroenterology, University Hospital, Nottingham, UK, 19 pages.
Liang, M. et al., "Identification and Characterization of a Potent, Selective, and Orally Active Antagonist of the CC Chemokine Receptor-1," *The Journal of Biological Chemistry*, Jun. 23, 2000, vol. 275, No. 25, pp. 19000-19008.
Liang, M. et al., "Species Selectivity of a small molecule antagonist for the CCR1 chemokine receptor," *European Journal of Pharmacology*, 2000, vol. 389, pp. 41-49.
Ng, H.P. et al., "Discovery of Novel Non-Peptide CCR1 Receptor Antagonists," *Journal of Medicinal Chemistry*, 1999, vol. 42, No. 22, pp. 4680-4694.
Palmer, A.M., "Pharmacotherapy for Alzheimer's disease: progress and prospects," *Trends in Pharmacological Sciences*, Sep. 2002, vol. 23, No. 9, pp. 426-433.
Penfold, M.E.T. et al., "Cytomegalovirus encodes a potent α chemokine," *Proc. Natl. Acad. Scie. USA*, Aug. 1999, vol. 96, pp. 9839-9844.
Podolin, P.L. et al. "A Potent and Selective Nonpeptide Anatagonist of CXCR2 Inhibits Acute and Chronic Models of Arthritis in the Rabbit," *The Journal of Immunology*, 2002, vol. 169, pp. 6435-6444.
Trentham, D.E. et al., "Autoimmunity to Type II Collagen: An Experimental Model of Arthritis," *The Journal of Experimental Medicine*, 1977, vol. 146, pp. 857-868.

* cited by examiner

*Primary Examiner*—Emily Bernhardt
(74) *Attorney, Agent, or Firm*—Townsend and Townsend and Crew LLP

(57) ABSTRACT

Compounds are provided that act as potent antagonists of the CCR1 receptor, and have in vivo anti-inflammatory activity. The compounds are 3-imidazoyl-pyrazolo[3,4-b]pyridine derivatives and are useful in pharmaceutical compositions, methods for the treatment of CCR1-mediated disease, and as controls in assays for the identification of competitive CCR1 antagonists.

6 Claims, No Drawings

3-(IMIDAZOLYL)-PYRAZOLO[3,4-B] PYRIDINES

CROSS-REFERENCES TO RELATED APPLICATIONS

This application claims the benefit of U.S. Provisional application Ser. No. 60/932,948, the content of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., Semin Immunol 11(2):95-104 (1999)). A hallmark of some demyelinating diseases such as multiple sclerosis is the chemokine-mediated monocyte/macrophage and T cell recruitment to the central nervous system (see, Kennedy, et al., J. Clin. Immunol. 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., Ann. Rev. Immunol. 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., Current Pharmaceutical Design 9:1201-1208 (2003)) since they have been implicated in rheumatoid arthritis, transplant rejection (see, DeVries, M. E., et al., ibid.), and multiple sclerosis (see, Fischer, et al., J Neuroimmunol. 110 (1-2):195-208 (2000); Izikson, et al., J. Exp. Med. 192(7): 1075-1080 (2000); and Rottman, et al., Eur. J. Immunol. 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., Immunol Lett. 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., J. Biol. Chem. 273(25): 15687-15692 (1998); Ng, et al., J. Med. Chem. 42(22):4680-4694 (1999); Liang, et al., J. Biol. Chem. 275(25):19000-19008 (2000); and Liang, et al., Eur. J. Pharmacol. 389(1):41-49 (2000)). In view of the effectiveness demonstrated for treatment of disease in animal models (see, Liang, et al., J. Biol. Chem. 275(25): 19000-19008 (2000)), the search has continued to identify additional compounds that can be used in the treatment of diseases mediated by CCR1 signaling.

BRIEF SUMMARY OF THE INVENTION

The present invention relates to compounds having formula I:

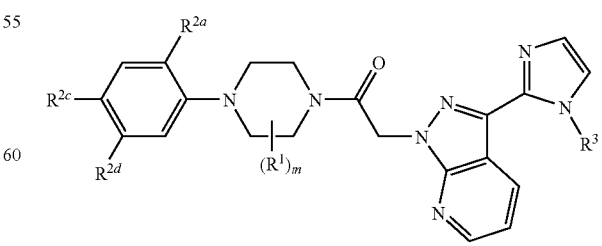

or pharmaceutically acceptable salts, hydrates or N-oxides thereof. In Formula I, $R^1$ is $C_{1-4}$ alkyl or $C_{1-4}$ haloalkyl, and the subscript m is an integer from 0 to 1. $R^{2a}$, $R^{2c}$, $R^{2d}$ are each members independently selected from the group consisting of hydrogen, halogen, $C_{1-4}$ alkoxy, $C_{1-4}$ alkyl, —O—$C_{1-4}$ haloalkyl and $C_{1-4}$ haloalkyl, and $R^3$ is a member selected from the group consisting of hydrogen and $C_{1-4}$ alkyl.

In addition to the compounds provided herein, the present invention further provides pharmaceutical compositions containing one or more of these compounds, as well as methods for the use of these compounds primarily to treat diseases associated with CCR1, CCR2 and/or CCR3 signalling activity.

BRIEF DESCRIPTION OF THE DRAWINGS

NONE

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-4}$ means one to four carbons). Examples of alkyl groups include methyl, ethyl, n-propyl, isopropyl, n-butyl, t-butyl, isobutyl, and sec-butyl.

The terms "alkoxy," is used in their conventional sense, and refer to those alkyl groups attached to the remainder of the molecule via an oxygen atom. Examples of alkoxy groups include methoxy, ethoxy, isopropoxy, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (BOC), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitroveratryloxycarbonyl (NVOC), and the like.

"Amino acid coupling reagent" refers to a reagent, such as HBTU (O-(benzotriazol-1-yl)-N,N,N',N'-tetramethyluronium hexafluorophosphate), etc., that will react with the carboxylic acid group of an amino acid to form an activated intermediate that can be used to condense with a wide variety of nucleophiles, for example, amines, alcohols and thiols, to produce other esters, thioesters or amides groups.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. General

The present invention derives from the discovery that compounds of formula I act as potent antagonists of the CCR1 receptor. The compounds have in vivo anti-inflammatory activity and have superior pharmacokinetic properties. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides for a compound of Formula I:

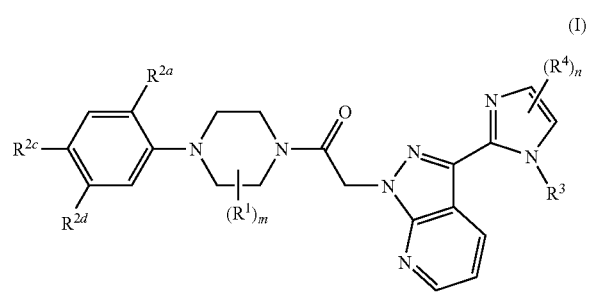

or pharmaceutically acceptable salt, hydrate or N-oxide thereof. In Formula I, $R^1$ is $C_{1-4}$ alkyl or $C_{1-4}$ haloalkyl, and the subscript m is an integer from 0 to 1. In Formula I, $R^{2a}$, $R^{2c}$, $R^{2d}$ are each a member independently selected from the group consisting of hydrogen, halogen, $C_{1-4}$ alkoxy, $C_{1-4}$ alkyl, —O—$C_{1-4}$ haloalkyl and $C_{1-4}$ haloalkyl; $R^3$ is a member selected from the group consisting of hydrogen and $C_{1-4}$ alkyl; and $R^4$ is $C_{1-4}$ alkyl, and the subscript n is an integer from 0-2. In one embodiment, $R^3$ is hydrogen. In another embodiment, $R^3$ is hydrogen and the subscript n is 0. In another embodiment, $R^1$ in Formula I is methyl, trifluoromethyl or ethyl and the subscript m is 1. In another embodiment the subscript m is 0. In yet another embodiment, $R^{2a}$, $R^{2c}$, and $R^{2d}$ are each independently selected from the group consisting of fluoro, chloro, bromo, iodo, methoxy, ethoxy, trifluoromethoxy, methyl, ethyl, trifluoromethyl and 2-fluoroethoxy. In yet another embodiment, $R^{2a}$ is hydrogen and $R^{2c}$ and $R^{2d}$ are each independently selected from the group consisting of fluoro, chloro, bromo, iodo, methoxy, ethoxy, trifluoromethoxy, methyl, ethyl, trifluoromethyl and 2-fluoroethoxy.

In one preferred embodiment, the compounds of the invention are of Formula Ia or Ib.

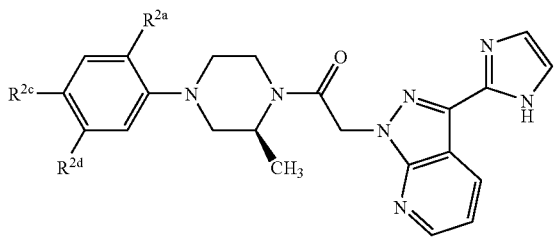

In one embodiment, $R^{2a}$ and $R^{2c}$ in Formula Ia or Ib, are each independently selected from the group consisting of fluoro, chloro, bromo and iodo; and $R^{2d}$ is selected from the group consisting of methoxy, ethoxy, trifluoromethoxy, methyl, ethyl, trifluoromethyl and 2-fluoroethoxy.

In a specific embodiment, compounds of Formula Ia or Ib are selected from the group consisting of:

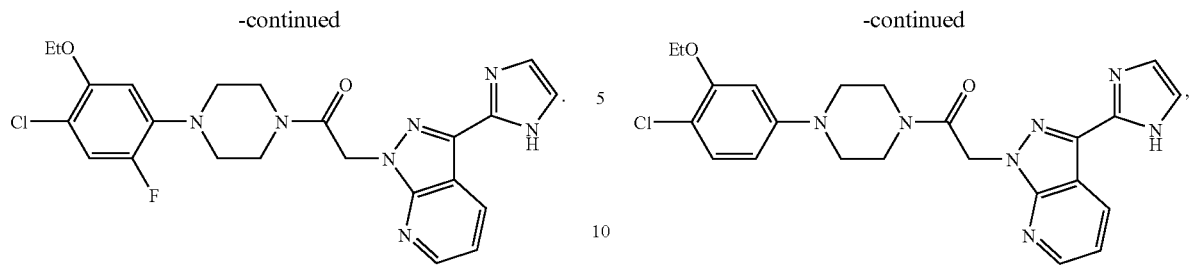

In another preferred embodiment, the compounds of the invention are of Formula Ic or Id:

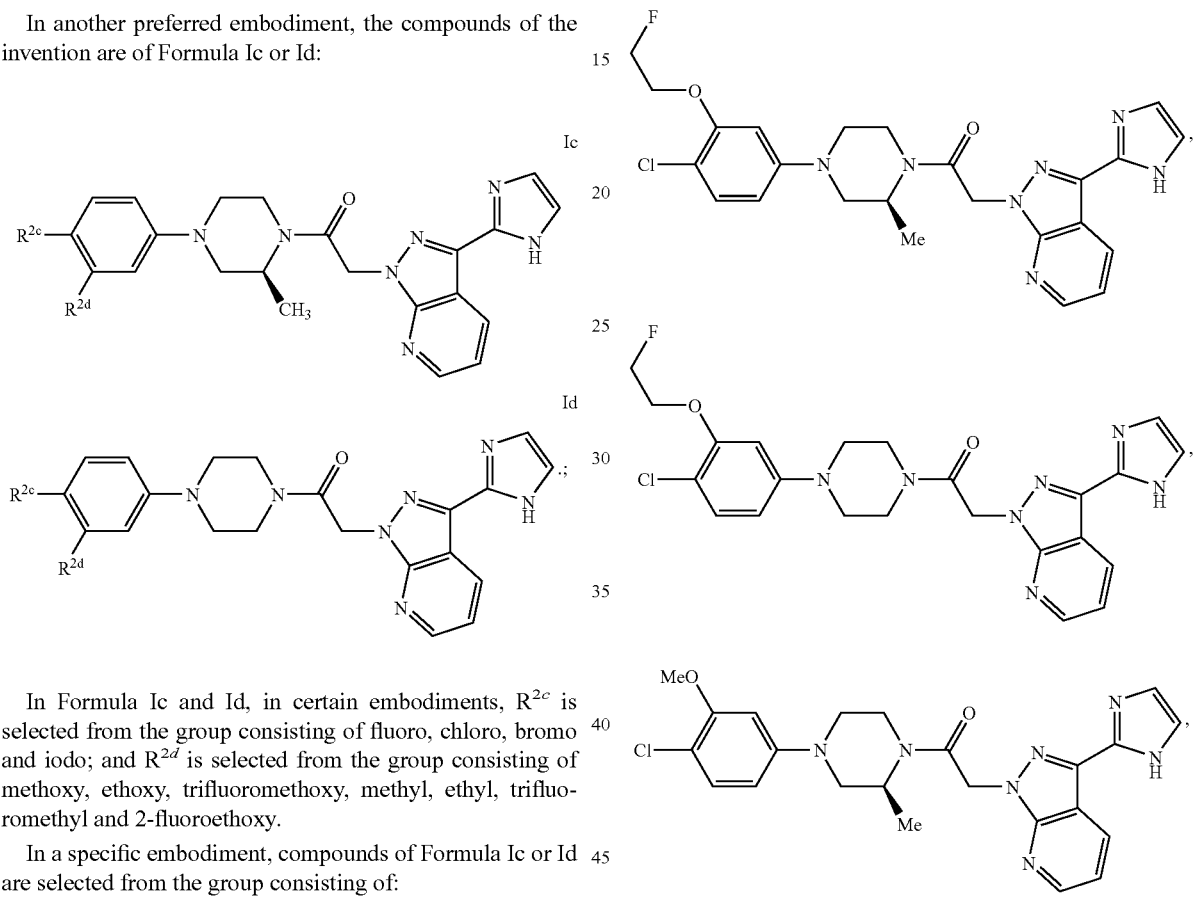

In Formula Ic and Id, in certain embodiments, $R^{2c}$ is selected from the group consisting of fluoro, chloro, bromo and iodo; and $R^{2d}$ is selected from the group consisting of methoxy, ethoxy, trifluoromethoxy, methyl, ethyl, trifluoromethyl and 2-fluoroethoxy.

In a specific embodiment, compounds of Formula Ic or Id are selected from the group consisting of:

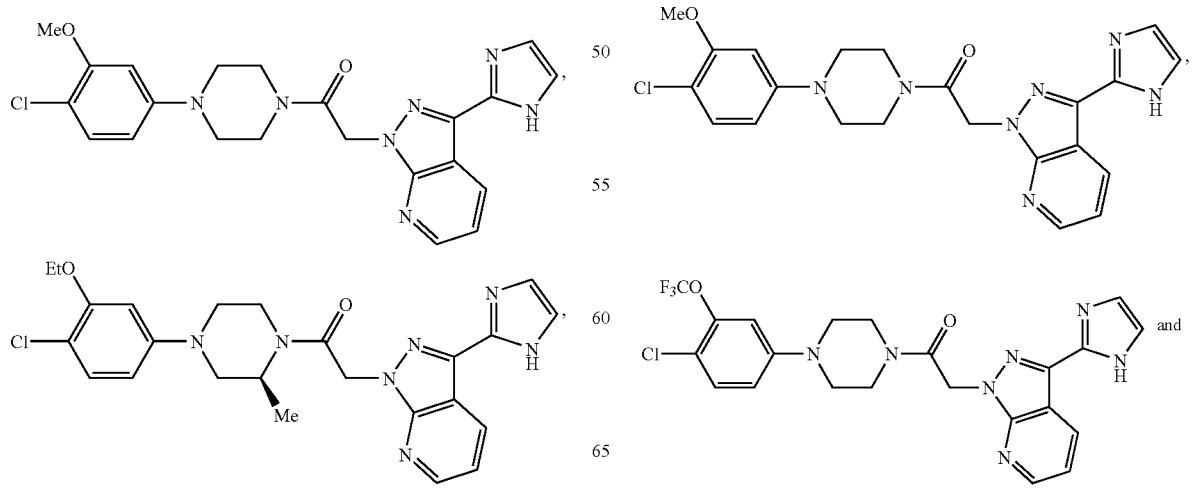

-continued

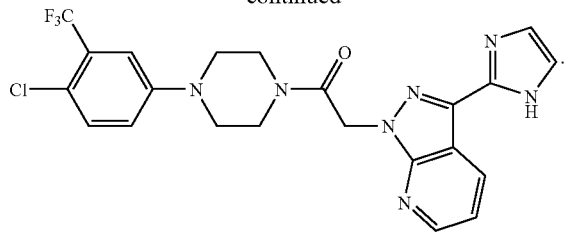

In yet another embodiment of the invention, the compound of Formula Id has the following structure:

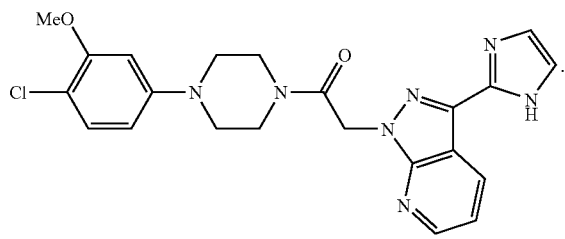

In still yet another embodiment, compounds of the invention of Formula I are selected from the group consisting of the compounds set forth in Table 1.

TABLE 1

1. 1-[4-(4-Chloro-3-methoxy-phenyl)-piperazin-1-yl]-2-[3-(1H-imidazol-2-yl)-pyrazolo[3,4-b]pyridin-1-yl]-ethanone
2. 1-[4-(4-Chloro-3-ethoxy-phenyl)-piperazin-1-yl]-2- [3-(1H-imidazol-2-yl)-pyrazolo[3,4-b]pyridin-1-yl]-ethanone
3. 1- {4-[4-Chloro-3-(2-fluoro-ethoxy)-phenyl]-piperazin-1-yl}-2-[3-(1H-imidazol-2-yl)-pyrazolo[3,4-b]pyridin-1-yl]-ethanone
4. 1-[4-(4-Chloro-3-methoxy-phenyl)-2-methyl-piperazin-1-yl]-2-[3-(1H-imidazol-2-yl)-pyrazolo[3,4-b]pyridin-1-yl]-ethanone
5. 1-[4-(4-Chloro-3-methoxy-phenyl)-3-methyl-piperazin-1-yl]-2-[3-(1H-imidazol-2-yl)-pyrazolo[3,4-b]pyridin-1-yl]-ethanone
6. 1-[4-(4-Chloro-3-trifluoromethyl-phenyl)-piperazin-1-yl]-2-[3-(1H-imidazol-2-yl)-pyrazolo[3,4-b]pyridin-1-yl]-ethanone
7. 1-[4-(4-Chloro-3-methoxy-phenyl)-piperazin-1-yl]-2-[3-(1-methyl-1H-imidazol-2-yl)-pyrazolo[3,4-b]pyridin-1-yl]-ethanone
8. 1-[4-(4-Chloro-2-fluoro-5-methoxy-phenyl)-piperazin-1-yl]-2-[3-(1H-imidazol-2-yl)-pyrazolo[3,4-b]pyridin-1-yl]-ethanone
9. 1-{4-[4-Chloro-3-(2-fluoro-ethoxy)-phenyl]-2-methyl-piperazin-1-yl}-2-[3-(1H-imidazol-2-yl)-pyrazolo[3,4-b]pyridin-1-yl]-ethanone
10. 1-[4-(4-Chloro-3-methoxy-phenyl)-2-methyl-piperazin-1-yl]-2-[3-(1H-imidazol-2-yl)-pyrazolo[3,4-b]pyridin-1-yl]-ethanone
11. 1-[4-(4-Chloro-5-ethoxy-2-fluoro-phenyl)-piperazin-1-yl]-2-[3-(1H-imidazol-2-yl)-pyrazolo[3,4-b]pyridin-1-yl]-ethanone
12. 1-[4-(4-Chloro-3-trifluoromethoxy-phenyl)-piperazin-1-yl]-2-[3-(1H-imidazol-2-yl)-pyrazolo[3,4-b]pyridin-1-yl]-ethanone
13. 1-[4-(4-Chloro-2-fluoro-5-methoxy-phenyl)-2-methyl-piperazin-1-yl]-2-[3-(1H-imidazol-2-yl)-pyrazolo[3,4-b]pyridin-1-yl]-ethanone
14. 1-[4-(4-Chloro-3-ethoxy-phenyl)-2-methyl-piperazin-1-yl]-2-[3-(1H-imidazol-2-yl)-pyrazolo[3,4-b]pyridin-1-yl]-ethanone
15. 1-{4-[4-Chloro-2-fluoro-5-(2-fluoro-ethoxy)-phenyl]-piperazin-1-yl}-2-[3-(1H-imidazol-2-yl)-pyrazolo[3,4-b]pyridin-1-yl]-ethanone
16. 1-[4-(4-Chloro-3-methoxy-phenyl)-3-methyl-piperazin-1-yl]-2-[3-(1H-imidazol-2-yl)-pyrazolo[3,4-b]pyridin-1-yl]-ethanone
17. 1-[4-(4-Chloro-3-methyl-phenyl)-piperazin-1-yl]-2-[3-(1H-imidazol-2-yl)-pyrazolo[3,4-b]pyridin-1-yl]-ethanone
18. 1-[4-(4-Chloro-2-fluoro-5-methoxy-phenyl)-2-methyl-piperazin-1-yl]-2-[3-(1H-imidazol-2-yl)-pyrazolo[3,4-b]pyridin-1-yl]-ethanone The compounds of the present invention exhibit superior pharmacokinetic properties over related compounds (see U.S. Publication No. 2007/0010524A1). More particularly, the present compounds, and particularly compound 1.016 (see Table 2) exhibits improved oral bioavailability, increased Cmax and increased AUC in tests conducted in animals.

Preparation of Compounds

The schemes below provide certain synthetic routes that can be followed to access certain compounds of the present invention. Other routes or modification of the routes presented below would be readily apparent to a skilled artisan and are within the scope of the present invention.

Scheme 1 illustrates the synthesis of 3-imidazolyl substituted pyrazolo[3,4-b]pyridines. R' represents a non-interfering substituent, such as, for example, a protecting group, or a carboxy ester. As shown in Scheme 1, the reaction of $NH_2OH$ with 3-cyano pyrazolo[3,4-b]pyridine i will provide the hydroxylamidine compound ii. Reduction of ii using hydrogen gas and a catalyst (e.g., Pd/C or $Pd(OH)_2$ will produce the amidine product iii. Cyclization of iii by treatment with chloroacetaldehyde will produce the imidazole product iv.

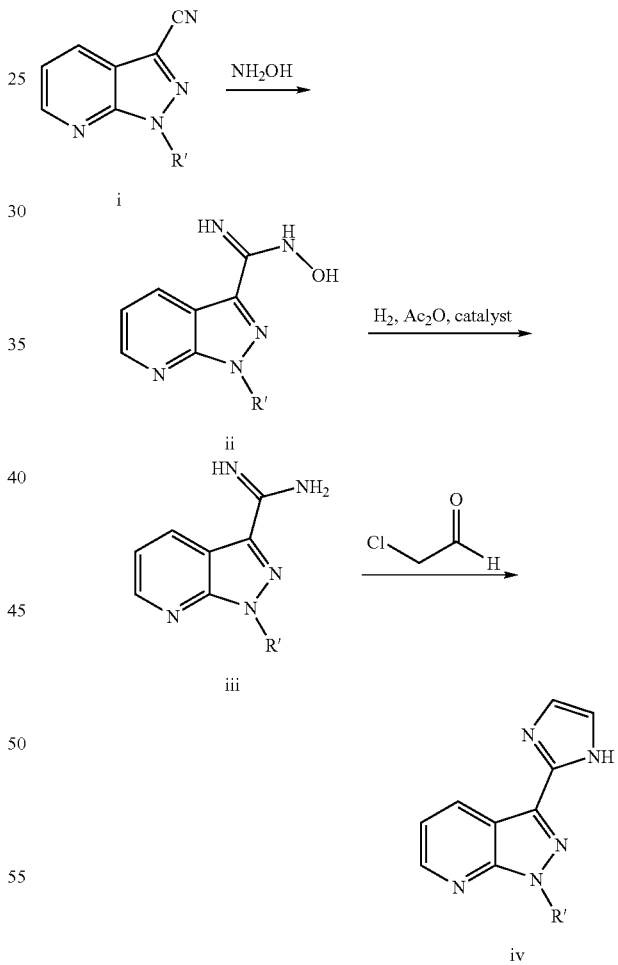

Scheme 2 illustrates the synthesis of 3-imidazolyl substituted pyrazolo[3,4-b]pyridines. R' represents a non-interfering substituent, such as, for example, a protecting group, or a carboxy ester. In Scheme 2, the reaction of 3-cyano-pyrazolo [3,4-b]pyridine with ethylene diamine produces the cyclized imidazoline product v, which upon oxidation will produce imidazole vi.

Scheme 2

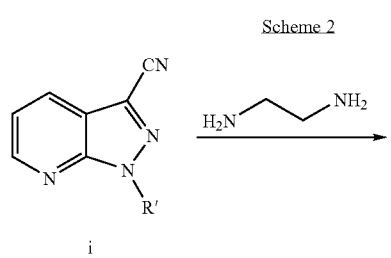

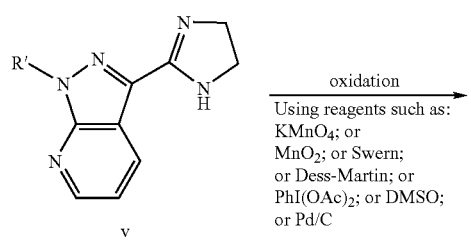

Scheme 3 illustrates the synthesis of 3-imidazolyl substituted pyrazolo[3,4-b]pyridines. R' represents a non-interfering substituent, such as, for example, a protecting group, or a carboxy ester, or the remainder of the compound of formula I (see also Example 18). As shown in Scheme 3, using a transmetallation process, 3-iodo-pyrazolo[3,4-b]pyridine vii can be converted to 3-formyl-pyrazolo[3,4-b]pyridine viii, which upon treatment with glyoxal, is cyclized to form 3-imidazolyl-pyrazolo[3,4]pyridine ix.

The amino acid coupling procedure that can be used to form compounds of the invention is illustrated in Scheme 4. In Scheme 4, R, R" represents non-interfering substitutents. The compounds of the invention can be prepared, for example, by coupling a carboxylic acid derivative of a 3-imidazolyl-pyrazolo[3,4-b]pyridine x with a piperazine derivative xi using any amino acid coupling reagent (e.g., HBTU, HATU, pyBOP, etc.) to form a 3-imidazolyl-pyrazolo[3,4-b]pyridine (xii) of the present invention.

III. Pharmaceutical Compositions

In addition the compounds provided above, the compositions for modulating CCR1, CCR2 and CCR3 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. patent application Ser. No. 5,833,651 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable copolymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

IV. Methods of Treating Diseases Modulated by CCR1, CCR2 and/or CCR3

In yet another aspect, the present invention provides methods of treating CCR1-, CCR2- and/or CCR3-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1, CCR2 or CCR3 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as asthma, allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, Takuyasu arthritis, rheumatoid arthritis, psoriatic arthritis, osteoarthritis, polyarticular arthritis, multiple sclerosis, systemic lupus erythematosus, type I diabetes, type II diabetes, type I diabetes (recent onset), optic neuritis, glomerulonephritis, and the like, (10) graft rejection including allograft rejection and acute and chronic graft-vs-host disease, (11) fibrosis (e.g. pulmonary fibrosis (i.e. idiopathic pulmonary fibrosis, interstitial pulmonary fibrosis), fibrosis associated with end-stage renal disease, fibrosis caused by radiation, tubulointerstitial fibrosis, subepithelieal fibrosis, scleroderma (progressive systemic sclerosis), hepatic fibrosis (including that caused by alcoholic or viral hepatitis), primary and secondary cirrhosis), (12) acute and chronic lung inflammation (chronic obstructive pulmonary disease, chronic bronchitis, adult respiratory distress syndrome, respiratory distress syndrome of infancy, immune complex alveolitis) and (13) other diseases in which undesired inflammatory responses or immune disorders are to be inhibited, such as cardiovascular disease including atherosclerosis, vascular inflammation resulting from tissue transplant or during restenosis (including, but not limited to restenosis following angioplasty and/or stent insertion), other acute and chronic inflammatory conditions such as myositis, neurodegenerative diseases (e.g., Alzheimer's disease), encephalitis, meningitis, hepatitis, nephritis, sepsis, sarcoidosis, allergic conjunctivitis, otitis, sinusitis, synovial inflammation caused by arthroscopy, hyperuremia, trauma, ischaemia reperfusion injury, nasal polyosis, preeclampsia, oral lichen planus, Guillina-Barre syndrome, granulomatous diseases, conditions associated with leptin production, Behcet's syndrome and gout and in wound healing applications (14) immune mediated food allergies such as Celiac disease.

In another group of embodiments, diseases or conditions can be treated with modulators of CCR1 function. Examples of diseases to be treated with modulators of CCR1 function include cancers (both primary and metastatic) (e.g., multiple myeloma; Hata, H., Leukemia & Lymphoma, 2005, 46(7); 967-972), cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Pharmaceutical compositions of this invention can also inhibit the production of metalloproteinases and cytokines at inflammatory sites, either directly or indirectly (as a consequence of decreasing cell infiltration) thus providing benefit for diseases or conditions linked to these cytokines.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, CX$_3$CR1 and CXCR6; (m) lubricants or emollients such as petrolatum and lanolin, (n) keratolytic agents (e.g., tazarotene), (o) vitamin D$_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

V. EXAMPLES

The following examples are offered to illustrate, but not to limit the claimed invention.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:

HPLC, High Pressure Liquid Chromatography; DMF, Dimethyl formamide; TFA, Trifluoroacetic Acid; THF, Tetrahydrofuran; EtOAc, Ethyl acetate; BOC$_2$O, di-tertbutyl dicarbonate or BOC anhydride; HPLC, High Pressure Liquid Chromatography; DIPEA, Diisopropyl ethylamine; HBTU, O-(benzotriazol-1-yl)-N,N,N',N'-tetramethyluronium hexafluorophosphate; dppf, 1,1'-Bis(diphenylphosphino)ferrocene; Pd$_2$(dba)$_3$, Tris(dibenzylideneacetone)dipalladium (0); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them. Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Synthesis of 1-[4-(4-Chloro-5-ethoxy-2-fluorophenyl)piperazin-1-yl]-2-[3-(1H-imidazol-2-yl)-pyrazolo[3,4-b]pyridin-1-yl]ethanone

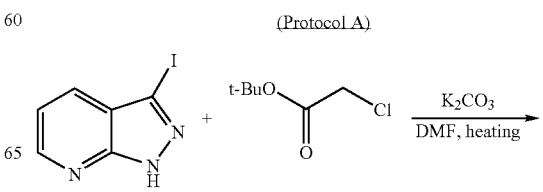

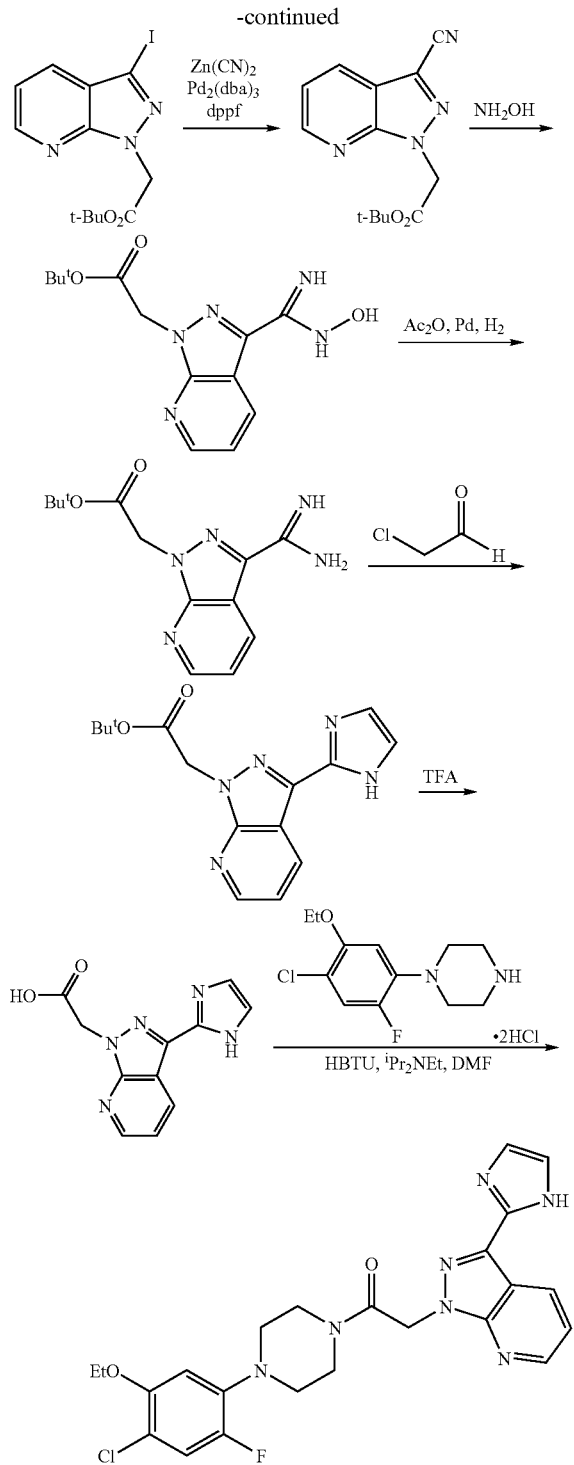

Step 1: A mixture of 3-iodo-7-azaindazole (25.50 g) and K₂CO₃ (41.4 g) in DMF (200 mL) was heated to 85° C. and t-butyl chloroacetate (14.3 mL) was slowly added. The mixture was stirred at this temperature for 1 hour (h), cooled to room temperature followed by the addition of water (300 mL). Filtration of the reaction mixture provided (3-iodo-pyrazolo[3,4-b]pyridin-1-yl)-acetic acid tert-butyl ester.

Step 2: A 250 mL flask was charged with (3-iodo-pyrazolo[3,4-b]pyridin-1-yl)-acetic acid tert-butyl ester (15.0 g), PdCl₂(dppf) (3.0 g), Zn(CN)₂ (4.96 g), DMF (200 mL) and H₂O (14 mL). The flask containing the resultant suspension was degassed and backfilled with nitrogen gas repeatedly for 5 minutes, followed by addition of Pd₂(dba)₃ (3.85 g) to the reaction mixture. The reaction mixture was heated under N₂ at 90° C. for 16 h, cooled to room temperature, diluted with H₂O (800 mL) and filtered. The collected solid was washed with toluene (10 mL) to provide (3-cyano-pyrazolo[3,4-b]pyridin-1-yl)-acetic acid tert-butyl ester as a yellow solid.

Step 3: A mixture of (3-cyano-pyrazolo[3,4-b]pyridin-1-yl)-acetic acid tert-butyl ester, hydroxylamine hydrochloride (8.28 g) and Et₃N (22.6 mL) in EtOH (120 mL) was heated over night under N₂ at 65° C. The resultant mixture was cooled to room temperature, filtered and the collected solid was washed with H₂O (100 mL) and Et₂O (50 mL×2) to afforded [3-(N-hydroxycarbamimidoyl)-pyrazolo[3,4-b]pyridin-1-yl]-acetic acid tert-butyl ester.

Step 4: [3-(N-Hydroxycarbamimidoyl)-pyrazolo[3,4-b]pyridin-1-yl]-acetic acid tert-butyl ester (6.17 g) in a 100 mL vial was charged with AcOH (45 mL) and Ac₂O (4.3 mL). The resultant mixture was stirred at room temperature for 1 h at this time the initial suspension became a clear solution. To this solution was added Pd/C (10%, 900 mg) and stirred under 1 atm H₂ balloon, and resultant mixture was stirred over night at room temperature. The reaction mixture was filtered through a pad of celite washed with DCM/MeOH. Evaporation of the solvent gave (3-amidino-pyrazolo[3,4-b]pyridin-1-yl)-acetic acid tert-butyl ester which was used without further purification.

Step 5: (3-Amidino-pyrazolo[3,4-b]pyridin-1-yl)-acetic acid tert-butyl ester obtained above in a 100 mL vial was charged with chloroacetylaldehyde (5.72 mL), dioxane (50 mL) and K₂CO₃ (12.42 g). The resultant mixture was stirred at 80° C. for 4 h and more chloroacetylaldehyde (5.72 mL) and K₂CO₃ (12.42 g) were added. The mixture was stirred another 1 h at 80° C. and stirred at 120° C. for another 1 h, cooled to room temperature, diluted with dichloromethane (DCM), washed with brine, dried (Na₂SO₄), filtered and evaporated in vacuo. Purification by flash chromatography provided 2-(3-(1H-imidazol-2-yl)-1H-pyrazolo[3,4-b]pyridin-1-yl)acetic acid tert-butyl ester as a brown oil.

Step 6: 2-(3-(1H-imidazol-2-yl)-1H-pyrazolo[3,4-b]pyridin-1-yl)acetic acid tert-butyl ester (977 mg) was dissolved in trifluoroacetic acid (TFA) (10 mL) and stirred at room temperature for 1 hr. The mixture was evaporated in vacuo to provide 2-(3-(1H-imidazol-2-yl)-1H-pyrazolo[3,4-b]pyridin-1-yl)acetic acid as a brown oil, which was used without further purification.

Step 7: (Protocol A—the HBTU coupling procedure) A solution of [3-(1H-imidazol-2-yl)-pyrazolo[3,4-b]pyridin-1-yl]acetic acid (0.30 M, 0.40 mL, 0.12 mmol) was transferred to a vial. 1-(4-Chloro-5-ethoxy-2-fluorophenyl)piperazine dihydrochloride (48 mg, 0.14 mmol), O-(benzotriazol-1-yl)-N,N,N',N'-tetramethyluronium hexafluorophosphate (HBTU) (55 mg, 0.14 mmol) and i-Pr₂NEt (0.30 mL) were added to the vial and the mixture was stirred at ambient temperature. After 30 minutes, LC/MS analysis indicated formation of desired product and complete consumption of the carboxylic acid starting material. The mixture was diluted with EtOAc, washed with water (1×) and brine (1×), dried over Na₂SO₄ and evaporated. The residue was purified by silica gel chromatography (1% to 8% MeOH in CH₂Cl₂) to provide 1-[4-(4-chloro-5-ethoxy-2-fluorophenyl)piperazin-1-yl]-2-[3-(1H-imidazol-2-yl)pyrazolo[3,4-b]pyridin-1-yl]ethanone as a tan solid: $^1$H NMR (CDCl₃, 400 MHz) δ8.79 (dd, 0.6H, J=8.4, 1.6 Hz), 8.66 (dd, 0.4H, J=8.0, 1.6 Hz), 8.57-8.55 (m, 1H), 7.29-7.26 (m, 1H), 7.22-7.16 (m, 1H), 7.09-7.05 (m, 2H), 6.50-6.45 (m, 2H), 5.45 (s, 0.6H), 5.43 (s, 1.4H), 4.07-4.01 (m, 2H), 3.81-3.69 (m, 4H), 3.17-3.13 (m, 1.6H), 3.08-3.02 (m, 2.4H), 1.50-1.42 (m, 3H); LC/MS m/z (M+H)+ 484.4.

Example 2

Synthesis of 1-{4-[4-Chloro-2-fluoro-5-(2-fluoroethoxy)-phenyl]piperazin-1-yl}-2-[3-(1H-imidazol-2-yl)-pyrazolo[3,4-b]pyridin-1-yl]ethanone

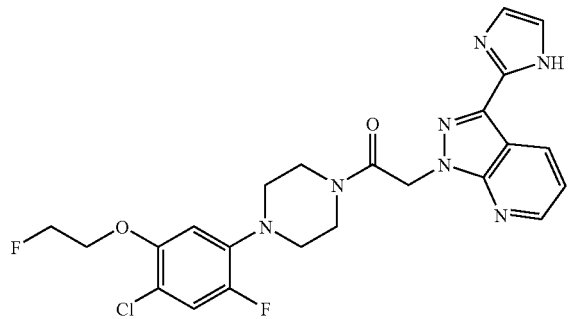

The title compound was prepared following Protocol A. 1-[4-Chloro-2-fluoro-5-(2-fluoroethoxy)phenyl]-piperazine dihydrochloride and [3-(1H-imidazol-2-yl)pyrazolo[3,4-b]pyridin-1-yl]acetic acid were used as the coupling components. The crude product was purified by silica gel chromatography (2% to 3.5% MeOH in CH$_2$Cl$_2$) to provide 1-{4-[4-chloro-2-fluoro-5-(2-fluoroethoxy)phenyl]piperazin-1-yl}-2-[3-(1H-imidazol-2-yl)pyrazolo[3,4-b]pyridin-1-yl]ethanone as a tan solid: $^1$H NMR (CDCl$_3$, 400 MHz) δ 8.79 (dd, 0.6H, J=8.0, 1.8 Hz), 8.67 (d, 0.4H, J=6.4 Hz), 8.57-8.55 (m, 1H), 7.30-7.25 (m, 1H), 7.11-7.06 (m, 2H), 6.63 (d, 0.6H, J=7.6 Hz), 6.57 (d, 0.4H, J=7.6 Hz), 6.54 (d, 1H, J=7.6 Hz), 5.45 (s, 0.7H), 5.43 (s, 1.3H), 4.83-4.80 (m, 1H), 4.71-4.68 (m, 1H), 4.31-4.18 (m, 2H), 3.82-3.76 (m, 3H), 3.50 (t, 1H, J=5.2 Hz), 3.23-3.04 (m, 4H); LC/MS m/z (M+H)+ 502.4.

Example 3

Synthesis of 1-[4-(4-Chloro-3-ethoxyphenyl)piperazin-1-yl]-2-[3-(1H-imidazol-2-yl)pyrazolo[3,4-b]pyridin-1-yl]ethanone

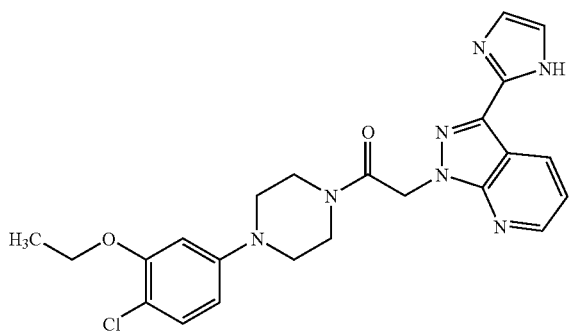

The title compound was prepared following Protocol A. 1-(4-Chloro-3-ethoxyphenyl)piperazine dihydrochloride and [3-(1H-imidazol-2-yl)pyrazolo[3,4-b]pyridin-1-yl]acetic acid were used as the coupling components. The crude product was purified by silica gel chromatography (4% to 15% MeOH in CH$_2$Cl$_2$) to provide 1-[4-(4-chloro-3-ethoxyphenyl)piperazin-1-yl]-2-[3-(1H-imidazol-2-yl)pyrazolo[3,4-b]pyridin-1-yl]ethanone as a tan solid (25 mg): $^1$H NMR (CDCl$_3$, 400 MHz) δ8.79 (dd, 0.6H), 8.66 (dd, 0.4H), 8.57-

8.54 (m, 1H), 7.29-7.19 (m, 4H), 6.49-6.40 (m, 2H), 5.45 (s, 0.7H), 5.43 (s, 1.3H), 4.10-4.04 (m, 2H), 3.81-3.69 (m, 4H), 3.23-3.16 (m, 4H), 1.50-1.45 (m, 3H); LC/MS m/z (M+H)+ 466.4.

Example 4

Synthesis of 1-[4-(4-Chloro-2-fluoro-5-methoxyphenyl)piperazin-1-yl]-2-[3-(1H-imidazol-2-yl)-pyrazolo[3,4-b]pyridin-1-yl]ethanone

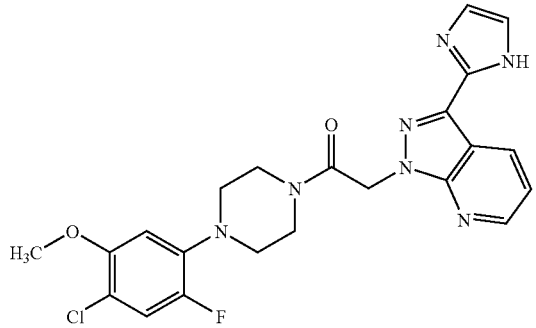

The title compound was prepared following Protocol A. 1-(4-Chloro-2-fluoro-5-methoxyphenyl)piperazine dihydrochloride and [3-(1H-imidazol-2-yl)-pyrazolo[3,4-b]pyridin-1-yl]-acetic acid were used as the coupling components. The crude product was purified by silica gel chromatography (1% to 10% MeOH in CH$_2$Cl$_2$) to provide 1-[4-(4-chloro-2-fluoro-5-methoxyphenyl)piperazin-1-yl]-2-[3-(1H-imidazol-2-yl)-pyrazolo[3,4-b]pyridin-1-yl]ethanone as a tan solid (27 mg): $^1$H NMR (CDCl$_3$, 400 MHz) δ8.79 (dd, 0.6H), 8.67 (dd, 0.4H), 8.57-8.55 (m, 1H), 7.31-7.20 (m, 2H), 7.12-7.06 (m, 2H), 6.49-6.45 (m, 1H), 5.45 (s, 0.6H), 5.43 (s, 1.4H), 3.86 (s, 0.9H), 3.85 (s, 2.1H), 3.81-3.75 (m, 4H), 3.15-3.08 (m, 4H); LC/MS m/z (M+H)+ 470.4.

Example 5

Synthesis of 1-[(S)-4-(4-Chloro-3-methoxyphenyl)-2-methylpiperazin-1-yl]-2-[3-(1H-imidazol-2-yl)-pyrazolo[3,4-b]pyridin-1-yl]ethanone

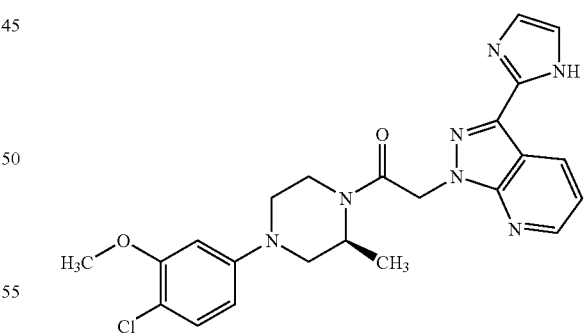

The title compound was prepared following Protocol A. (S)-1-(4-Chloro-3-methoxyphenyl)-3-methylpiperazine dihydrochloride and [3-(1H-imidazol-2-yl)pyrazolo[3,4-b]pyridin-1-yl]acetic acid were used as the coupling components. The crude product was purified by silica gel chromatography (1% to 8% MeOH in CH$_2$Cl$_2$) to provide 1-[(S)-4-(4-chloro-3-methoxyphenyl)-2-methylpiperazin-1-yl]-2-[3-(1H-imidazol-2-yl)-pyrazolo[3,4-b]pyridin-1-yl]ethanone as a tan solid: $^1$H NMR (CDCl$_3$, 400 MHz) δ 8.79 (dd, 0.6H), 8.66 (dd, 0.4H), 8.57-8.55 (m, 1H), 7.29-7.19 (m, 4H), 6.44-

6.39 (m, 2H), 5.42 (br. s, 2H), 4.83 (br. s, 0.3H), 4.49 (br. s, 0.3H), 4.30 (br. s, 0.3H), 3.89 (s, 1.2H), 3.88 (s, 1.8H), 3.83 (br. s, 0.3H), 3.72-3.69 (m, 1H), 3.54-3.52 (m, 1H), 3.38 (br. s, 1H), 3.19-3.15 (m, 1H), 3.00 (br. s, 1H), 2.80 (br. s, 1H), 1.50-1.43 (m, 3H); LC/MS m/z (M+H)$^+$ 466.4.

Example 6

Synthesis of 1-[(S)-4-(4-Chloro-2-fluoro-5-methoxyphenyl)-2-methylpiperazin-1-yl]-2-[3-(1H-imidazol-2-yl)pyrazolo[3,4-b]pyridin-1-yl]ethanone

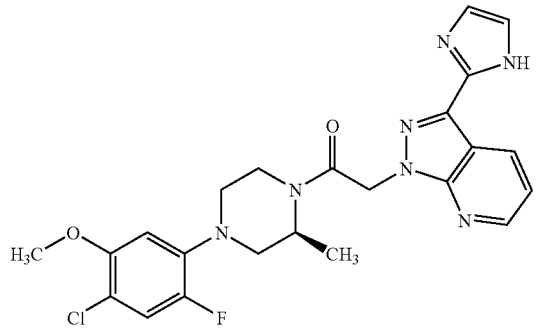

The title compound was prepared following Protocol A. (S)-1-(4-Chloro-2-fluoro-5-methoxy-phenyl)-3-methylpiperazine dihydrochloride and [3-(1H-imidazol-2-yl)pyrazolo[3,4-b]pyridin-1-yl]acetic acid were used as the coupling components. The crude product was purified by silica gel chromatography (2% to 3% MeOH in CH$_2$Cl$_2$) to provide 1-[(S)-4-(4-chloro-2-fluoro-5-methoxyphenyl)-2-methylpiperazin-1-yl]-2-[3-(1H-imidazol-2-yl)pyrazolo[3,4-b]pyridin-1-yl]ethanone as a tan solid (29 mg): $^1$H NMR (CDCl$_3$, 400 MHz) δ 8.79 (dd, 1H), 8.55 (dd, 1H), 7.27-7.21 (m, 3H), 7.07 (d, 1H), 6.43 (br. d, 1H), 5.46-5.37 (m, 2H), 4.83 (br. s, 0.3H), 4.51-4.48 (m, 0.6H), 4.28-4.21 (m, 0.6H), 3.86 (s, 0.9H), 3.85 (s, 2.1H), 3.79 (br. s, 0.3H), 3.67 (br. s, 0.3H), 3.33-3.21 (m, 2.5H), 2.95-2.93 (m, 0.9H), 2.83-2.76 (m, 1.6H), 1.48-1.40 (m, 3H); LC/MS m/z (M+H)$^+$ 484.4.

Example 7

Synthesis of 1-[(R)-4-(4-Chloro-3-methoxyphenyl)-3-methylpiperazin-1-yl]-2-[3-(1H-imidazol-2-yl)-pyrazolo[3,4-b]pyridin-1-yl]ethanone

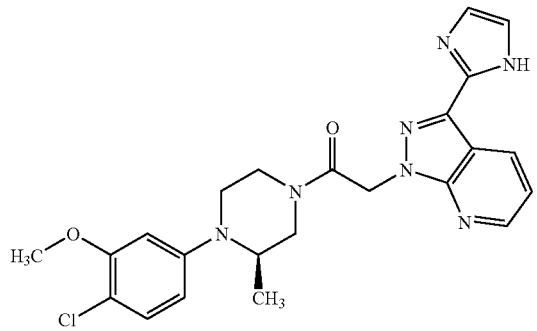

The title compound was prepared following Protocol A. (R)-1-(4-Chloro-3-methoxyphenyl)-2-methylpiperazine and [3-(1H-imidazol-2-yl)pyrazolo[3,4-b]pyridin 1-yl]acetic acid were used as the coupling components. The crude product was purified by silica gel chromatography (1% to 7.5% MeOH in CH$_2$Cl$_2$) to provide 1-[(R)-4-(4-chloro-3-methoxyphenyl)-3-methylpiperazin-1-yl]-2-[3-(1H-imidazol-2-yl)-pyrazolo[3,4-b]pyridin-1-yl]ethanone as a tan solid: $^1$H NMR (CDCl$_3$, 400 MHz) δ 8.76 (d, 0.6H), 8.66 (dd, 0.3H), 8.57-8.54 (m, 1H), 7.29-7.19 (m, 4H), 6.48-6.40 (m, 2H), 5.53-5.40 (m, 2H), 4.26 (br. d, 0.6H), 4.00 (br. d, 0.6H), 3.88 (s, 1.3H), 3.86 (s, 1.7H), 3.80-3.49 (m, 3.2H), 3.33 (br. s, 0.6H), 3.17-3.14 (m, 2H), 1.51-1.42 (m, 3H); LC/MS m/z (M+H)$^+$ 466.4.

Example 8

Synthesis of 1-[(S)-4-(4-Chloro-3-methoxyphenyl)-3-methylpiperazin-1-yl]-2-[3-(1H-imidazol-2-yl)-pyrazolo[3,4-b]pyridin-1-yl]ethanone

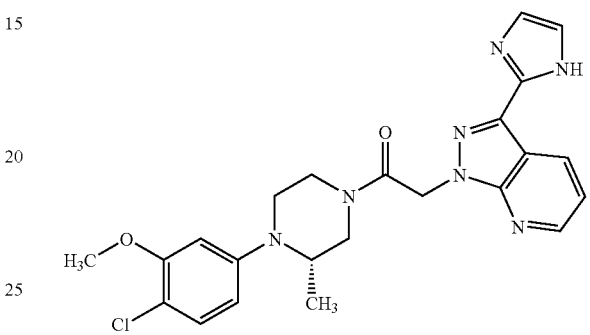

The title compound was prepared following protocol A. (S)-1-(4-Chloro-3-methoxyphenyl)-2-methylpiperazine and [3-(1H-imidazol-2-yl)pyrazolo[3,4-b]pyridin-1-yl]acetic acid were used as the coupling components. The crude product was purified by silica gel chromatography (1% to 7% MeOH in CH$_2$Cl$_2$) to provide 1-[(S)-4-(4-chloro-3-methoxyphenyl)-3-methylpiperazin-1-yl]-2-[3-(1H-imidazol-2-yl)-pyrazolo[3,4-b]pyridin-1-yl]ethanone as a tan solid: $^1$H NMR (CDCl$_3$, 400 MHz) δ 8.77 (d, 0.6H), 8.66 (d, 0.3H), 8.57-8.54 (m, 1H), 7.30-7.19 (m, 4H), 6.48-6.40 (m, 2H), 5.54-5.36 (m, 2H), 4.25 (br. d, 0.6H), 4.00 (br. d, 0.6H), 3.88 (s, 1.3H), 3.86 (s, 1.7H), 3.82-3.48 (m, 3.2H), 3.36-3.29 (m, 0.6H), 3.17-3.13 (m, 2H), 1.51-1.43 (m, 3H); LC/MS m/z (M+H)$^+$ 466.4.

Example 9

Synthesis of 1-[(R)-4-(4-Chloro-3-methoxyphenyl)-2-methylpiperazin-1-yl]-2-[3-(1H-imidazol-2-yl)-pyrazolo[3,4-b]pyridin-1-yl]ethanone

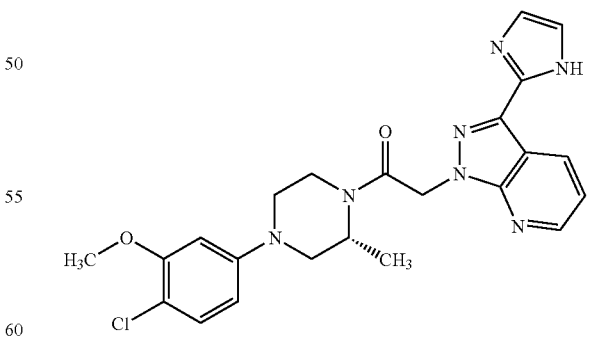

The title compound was prepared following Protocol A. (R)-1-(4-Chloro-3-methoxyphenyl)-3-methylpiperazine and [3-(1H-imidazol-2-yl)-pyrazolo[3,4-b]pyridin-1-yl]acetic acid were used as the coupling components. The crude product was purified by silica gel chromatography (1% to 7.5% MeOH in CH$_2$Cl$_2$) to provide 1-[(R)-4-(4-chloro-3-methoxyphenyl)-2-methylpiperazin-1-yl]-2-[3-(1H-imidazol-2-yl)- pyrazolo[3,4-b]pyridin-1-yl]ethanone as a tan solid: $^1$H NMR (CDCl$_3$, 400 MHz) δ 8.75 (d, 0.6H), 8.66 (dd, 0.4H), 8.57-8.54 (m, 1H), 7.29-7.18 (m, 4H), 6.44-6.39 (m, 2H), 5.42 (br. s, 2H), 4.82 (br. s, 0.3H), 4.45 (br. s, 0.3H), 4.33 (br. s, 0.3H), 3.88 (s, 1.2H), 3.87 (s, 1.8H), 3.83 (br. s, 0.3H), 3.73-3.67 (m, 1H), 3.54-3.52 (m, 1H), 3.38 (br. s, 1H), 3.17-3.13 (m, 1H), 2.99 (br. s, 1H), 2.80 (br. s, 1H), 1.50-1.42 (m, 3H); LC/MS m/z (M+H)$^+$ 466.4.

Example 10

Synthesis of 2-(3-(1H-imidazol-2-yl)-1H-pyrazolo[3,4-b]pyridin-1-yl)-1-((S)-4-(4-chloro-3-ethoxyphenyl)-2-methylpiperazin-1-yl)ethanone

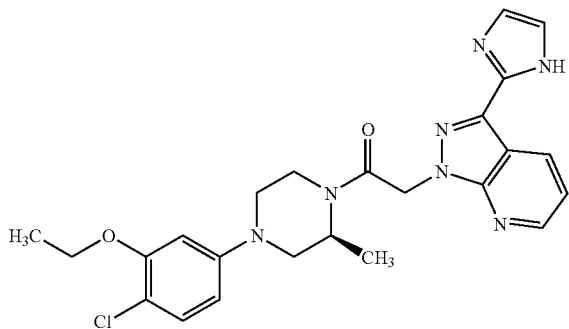

The title compound was prepared following Protocol A. To a vial containing (S)-1-(4-chloro-3-ethoxyphenyl)-3-methylpiperazine dihydrochloride (70 mg, 0.21 mmol) was added 2-(3-(1H-imidazol-2-yl)-1H-pyrazolo[3,4-b]pyridin-1-yl)acetic acid (51 mg, 0.21 mmol), HBTU (81 mg, 0.21 mmol), DMF (0.7 mL), and DIPEA (0.15 mL, 0.87 mmol). The reaction mixture was maintained at 30° C. for 24 h. The solution was diluted with EtOAc (30 mL) and washed with 1N HCl (2×10 mL) and sat. aq. NaCl (2×10 mL). The organic phase was dried over MgSO$_4$ and concentrated in vacuo. The resulting residue was purified by preparative HPLC (20→95% gradient of MeCN—H$_2$O with 0.1% TFA) and the pure fractions lyophilized to afford the indicated compound (11 mg, 11% yield): MS (ES) [M+H]+expected 480.2, found 480.5; $^1$H NMR (CDCl$_3$, 400 MHz) δ 9.94 (br s, 1H), 8.79 (dd, J=1.6, 8.0, 1H), 8.55 (dd, J=1.6, 4.4, 1H), 7.19-7.26 (m, 4H), 6.37-6.43 (m, 2H), 5.40 (br s, 2H), 2.78-4.81 (m, 10H), 4.07 (q, J=6.8, 2H), 1.46 (t, J=6.8, 3H).

Example 11

Synthesis of 2-(3-(1H-imidazol-2-yl)-1H-pyrazolo[3,4-b]pyridin-1-yl)-1-(4-(3-(2-fluoroethoxy)-4-chlorophenyl)piperazin-1-yl)ethanone

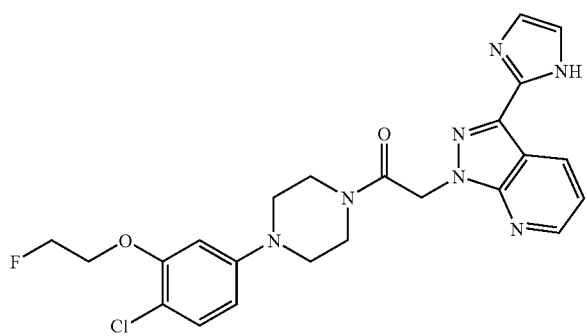

To a vial containing 1-(3-(2-fluoroethoxy)-4-chlorophenyl)piperazine dihydrochloride (70 mg, 0.21 mmol) was added 2-(3-(1H-imidazol-2-yl)-1H-pyrazolo[3,4-b]pyridin-1-yl)acetic acid (51 mg, 0.21 mmol), HBTU (83 mg, 0.22 mmol), DMF (0.7 mL), and DIPEA (0.20 mL, 1.2 mmol). The reaction mixture was maintained at 20° C. for 24 h. The solution was diluted with EtOAc (30 mL) and washed with 1N HCl (2×10 mL) and sat. aq. NaCl (2×10 mL). The organic phase was dried over MgSO$_4$ and concentrated in vacuo. The resultant residue was purified by preparative HPLC (20→95% gradient of MeCN—H$_2$O with 0.1% TFA) and the pure fractions lyophilized to afford the indicated compound (20 mg, 20% yield): MS (ES) [M+H]+expected 484.2, found 484.4; $^1$H NMR (CDCl$_3$, 400 MHz) d 9.94 (br s, 1H), 8.78 (dd, J=1.2, 8, 1H), 8.55 (dd, J=1.2, 4.6, 1H), 7.16-7.26 (m, 4H), 6.45-6.53 (m, 2H), 5.44 (s, 2H), 4.77 (dt, J=4.0, 46.8, 2H), 4.26 (dt, J=4.0, 26.8, 2H), 3.69-3.78 (m, 4H), 3.10-3.21 (m, 4H).

Example 12

Synthesis of 2-(3-(1H-imidazol-2-yl)-1H-pyrazolo[3,4-b]pyridin-1-yl)-1-((S)-4-(3-(2-fluoroethoxy)-4-chlorophenyl)-2-methylpiperazin-1-yl)ethanone

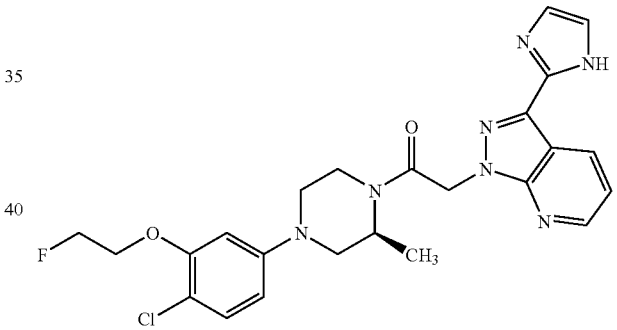

To a vial containing (S)-1-(3-(2-fluoroethoxy)-4-chlorophenyl)-3-methylpiperazine dihydrochloride (80 mg, 0.23 mmol) was added 2-(3-(1H-imidazol-2-yl)-1H-pyrazolo[3,4-b]pyridin-1-yl)acetic acid (51 mg, 0.21 mmol), HBTU (81 mg, 0.21 mmol), DMF (0.7 mL), and DIPEA (0.2 mL, 1.2 mmol). The reaction mixture was maintained at 30° C. for 24 h. The solution was diluted with EtOAc (30 mL) and washed with 1N HCl (2×10 mL) and sat. aq. NaCl (2×10 mL). The organic phase was dried over MgSO$_4$ and concentrated in vacuo. The resultant residue was purified by preparative HPLC (20→95% gradient of MeCN—H$_2$O with 0.1% TFA) and the pure fractions were lyophilized to afford the indicated compound (14 mg, 13% yield): MS (ES) [M+H]+expected 498.2, found 498.4; $^1$H NMR (CDCl$_3$, 400 MHz) δ 9.95 (br s, 1H), 8.79 (dd, J=1.6, 8.2, 1H), 8.55 (dd, J=1.6, 4.4, 1H), 7.19-7.26 (m, 4H), 6.44-6.50 (m, 2H), 5.40 (br s, 2H), 4.77 (dt, J=4.2, 47.2, 2H), 4.26 (dt, J=4.2, 27.2, 2H), 2.78-4.42 (m, 10H).

Example 13

Synthesis of 1-[4-(4-Chloro-3-methyl-phenyl)-piperazin-1-yl]-2-[3-(1H-imidazol-2-yl)-pyrazolo[3,4-b]pyridin-1-yl]-ethanone

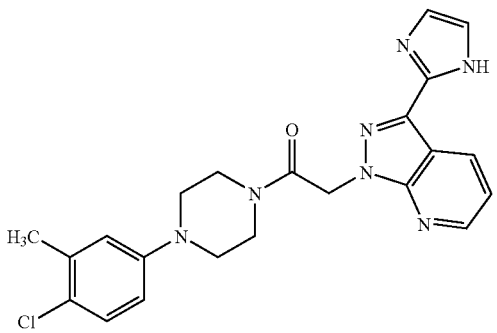

A vial was charged with 2-(3-(1H-imidazol-2-yl)-1H-pyrazolo[3,4-b]pyridin-1-yl)acetic acid (55 mg, 0.226 mmol), HBTU (125 mg, 0.33 mmol), 1-(4-Chloro-3-methyl-phenyl)-piperazine dihydrochloride (142 mg, 0.50 mmol), anhydrous DMF (2.0 mL), and DIPEA (0.5 mL). The vial was capped, heated to 45° C., and stirred overnight. The following day, the volatiles were removed in vacuo and separation by preparative hplc (reverse phase, acetonitrile-water gradient) gave 1-[4-(4-Chloro-3-methyl-phenyl)-piperazin-1-yl]-2-[3-(1H-imidazol-2-yl)-pyrazolo[3,4-b]pyridin-1-yl]-ethanone: MS (ES) [M+H]$^+$ found: 436.4

Example 14

Synthesis of 1-[4-(4-Chloro-3-trifluoromethyl-phenyl)-piperazin-1-yl]-2-[3-(1H-imidazol-2-yl)-pyrazolo[3,4-b]pyridin-1-yl]-ethanone

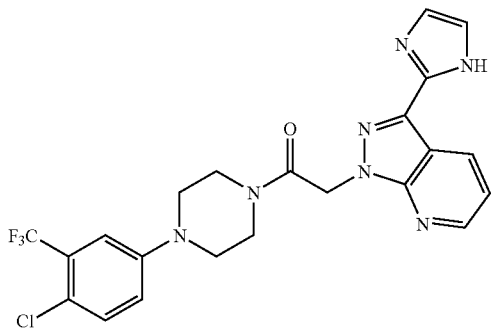

A vial was charged with 2-(3-(1H-imidazol-2-yl)-1H-pyrazolo[3,4-b]pyridin-1-yl)acetic acid (55 mg, 0.226 mmol), HBTU (125 mg, 0.33 mmol), 1-(4-Chloro-3-trifluoromethyl-phenyl)-piperazine dihydrochloride (170 mg, 0.50 mmol), anhydrous DMF (2.0 mL), and DIPEA (0.5 mL). The vial was capped, heated to 45° C., and stirred overnight. The following day, the volatiles were removed in vacuo and separation by preparative hplc (reverse phase, acetonitrile-water gradient) gave 1-[4-(4-Chloro-3-trifluoromethyl-phenyl)-piperazin-1-yl]-2-[3-(1H-imidazol-2-yl)-pyrazolo[3,4-b]pyridin-1-yl]-ethanone: MS (ES) [M+H]$^+$ found: 490.4

Example 15

Synthesis of 1-[4-(4-Chloro-3-trifluoromethoxyphenyl)-piperazin-1-yl]-2-[3-(1H-imidazol-2-yl)-pyrazolo[3,4-b]pyridin-1-yl]-ethanone

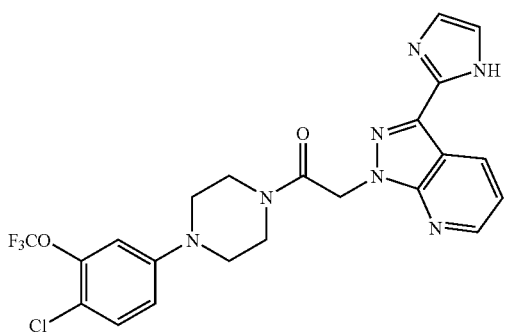

A vial was charged with 2-(3-(1H-imidazol-2-yl)-1H-pyrazolo[3,4-b]pyridin-1-yl)acetic acid (55 mg, 0.226 mmol), HBTU (125 mg, 0.33 mmol), 1-(4-Chloro-3-trifluoromethoxy-phenyl)-piperazine dihydrochloride (177 mg, 0.50 mmol), anhydrous DMF (2.0 mL), and DIPEA (0.4 mL). The vial was capped, heated to 45° C., and stirred overnight. The following day, the volatiles were removed in vacuo and separation by preparative hplc (reverse phase, acetonitrile-water gradient) gave 1-[4-(4-Chloro-3-trifluoromethoxyphenyl)-piperazin-1-yl]-2-[3-(1H-imidazol-2-yl)-pyrazolo[3,4-b]pyridin-1-yl]-ethanone. MS (ES) [M+H]$^+$ found: 506.4

Example 16

Synthesis of 1-[4-(4-Chloro-3-methoxy-phenyl)-piperazin-1-yl]-2-[3-(1H-imidazol-2-yl)-pyrazolo[3,4-b]pyridin-1-yl]-ethanone

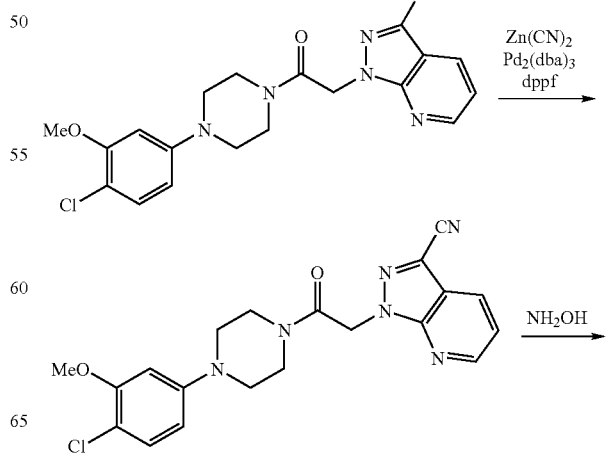

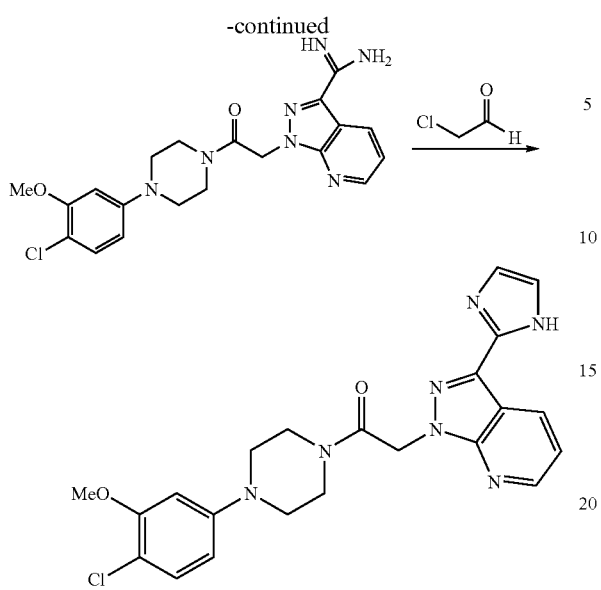
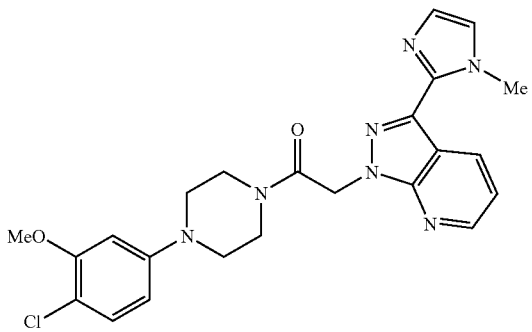

The title compound was prepared from 1-[4-(4-Chloro-3-methoxy-phenyl)-piperazin-1-yl]-2-[3-iodo-pyrazolo[3,4-b]pyridin-1-yl]-ethanone (see U.S. application Ser. No. 11/474,132, published as U.S. 20070010524, incorporated by reference) according to the procedure similar to those described from step 2 to step 5 in the synthesis of Example 1: $^1$H NMR (CDCl$_3$, 400 MHz) δ 10.22 (br, 1H), 8.82 (dd, 1H), 8.56 (dd, 1H), 7.20-7.30 (m, 3H), 7.11 (s, 1H), 6.47 (d, 1H), 6.42 (dd, 1H), 5.44 (s, 2H), 3.88 (s, 3H), 3.80 (m, 4H), 3.19 (m, 4H); MS (ES) M+H expect 452.2.

Example 17

Synthesis of 1-[4-(4-Chloro-3-methoxy-phenyl)-piperazin-1-yl]-2-[3-(1-methyl-1H-imidazol-2-yl)-pyrazolo[3,4-b]pyridin-1-yl]-ethanone To the solution of 1-[4-(4-Chloro-3-methoxy-phenyl)-piperazin-1-yl]-2-[3-(1H-imidazol-2-yl)-pyrazolo[3,4-b]pyridin-1-yl]-ethanone (50 mg, 0.11 mmol, 1 eq) in THF was added 60% sodium hydride (5.7 mg, 0.14 mmol, 1.3 eq) and stirred for 1 hr, followed by the addition of iodomethane (25.8 mg, 0.16 mmol, 1.5 eq). 2 hrs later, LCMS indicated that the major peak is the desired product. preparative hplc (reverse phase, acetonitrile-water gradient) gave 1-[4-(4-Chloro-3-methoxy-phenyl)-piperazin-1-yl]-2-[3-(1-methyl-1H-imidazol-2-yl)-pyrazolo[3,4-b]pyridin-1-yl]-ethanone. MS (ES) [M+H]$^+$ found: 465.2.

Example 18

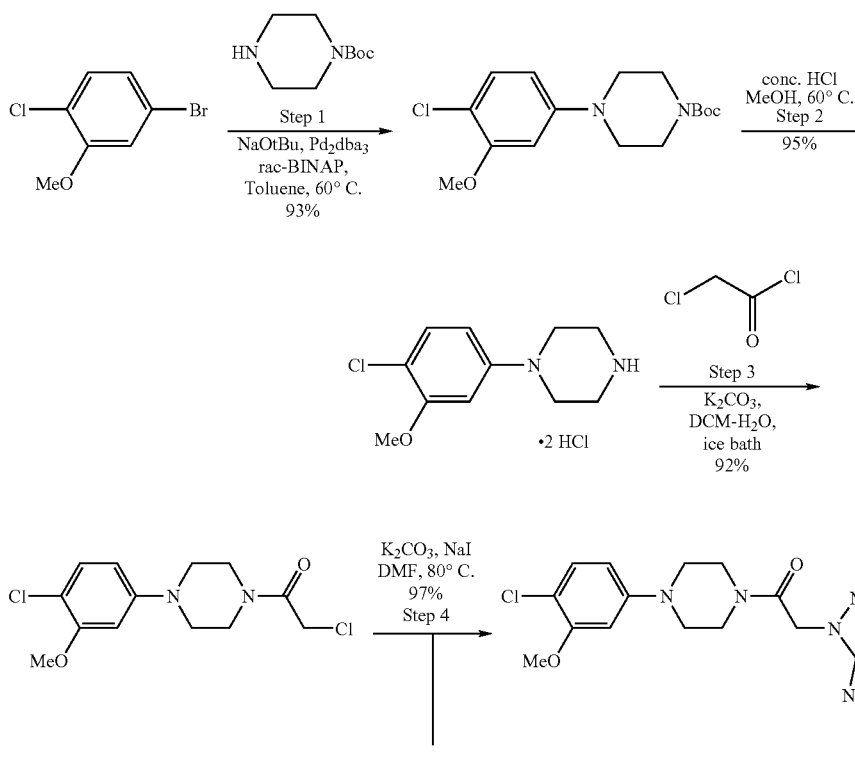

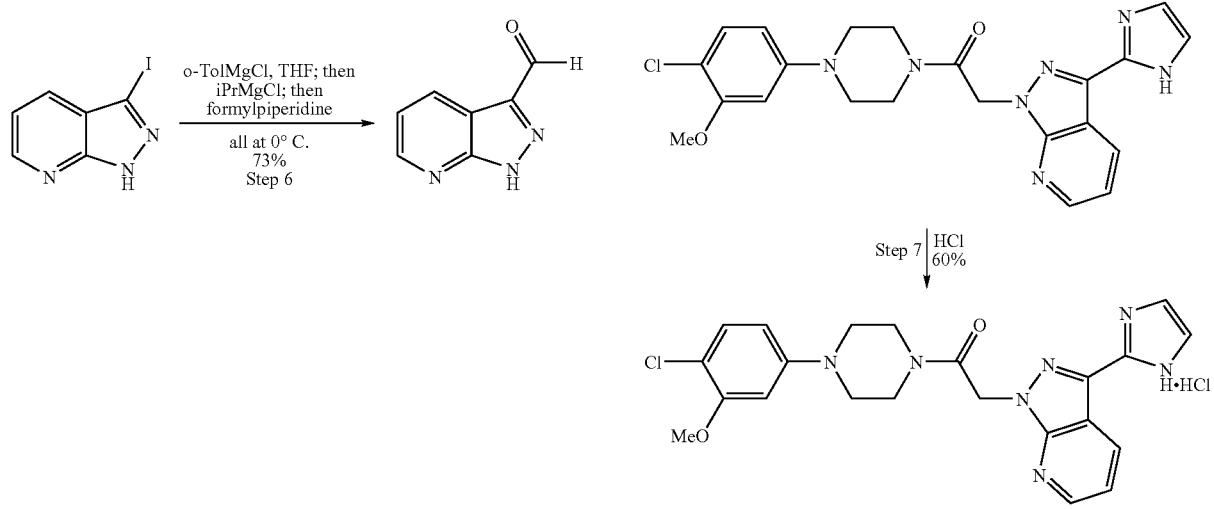

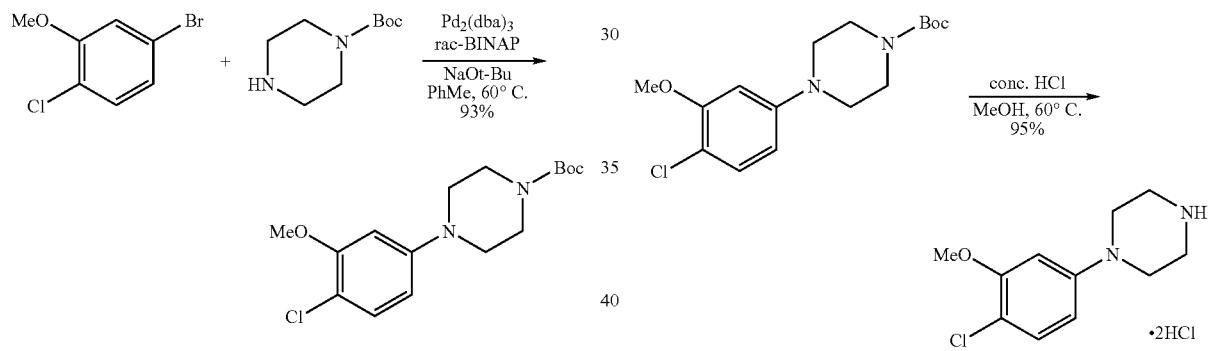

Step 1: Tert-butyl 4-(4-chloro-3-methoxyphenyl)piperazine-1-carboxylate

Step 2: 1-(4-chloro-3-methoxyphenyl)piperazine dihydrochloride

To a 3-necked, 5-L Morton flask equipped with a mechanical stirrer, gas adapter, heating mantle and thermometer was added rac-BINAP (4.24 g, 0.005 equiv) and Pd$_2$(dba)$_3$ (3.20 g, 0.0025 equiv). The flask was evacuated, and back-filled with nitrogen. Toluene (100 mL) was added by cannula. The mixture was stirred at room temperature for 15 min to give a purple solution. Toluene (2.0 L) was then added. 2-Chloro-5-bromoanisole (300.3 g, 1.356 mol, 1 equiv) was added in one portion. Boc-piperazine (252.4 g, 1 equiv) was added in one portion. Sodium tert-butoxide (183.0 g, 1.4 equiv) was added in one portion. The flask was evacuated and back-filled with nitrogen. The mixture was then heated to an internal temperature of 60° C. A heterogeneous light-orange slurry was obtained. After 1 h, the mixture becomes a homogeneous brown solution. After an additional 15 h, the mixture was cooled to room temperature. EtOAc (2.0 L) was added to the stirring mixture. The solid was filtered. The filtrate was washed with EtOAc (100 mL). The combined filtrate was washed with 10% aq. K$_2$CO$_3$ solution (1×1 L), water (1×1 L), and dried over MgSO$_4$. The solvent was removed in vacuo to afford the product as an orange solid (410.3 g, 93% yield).

A 4-L beaker equipped with a mechanical stirrer was charged with tert-butyl 4-(4-chloro-3-methoxyphenyl)piperazine-1-carboxylate (500 g, 1.53 mol, 1 equiv) and MeOH (1.50 L). While stirring at room temperature conc. 37% HCl (500 mL, 4 equiv) was added over 5 min. The internal temperature rose to 40° C., and the solution became thick with precipitate. After 15 min, the mixture was heated to an internal temperature of 60° C. on a hotplate. (Foaming begun at approximately 50° C. as the mixture warms.) After 2 h at 60° C., the solution was cooled to room temperature, and subsequently to 5° C. in a refrigerator. The product was collected by filtration in two batches. Each batch of the red-brown filtrate was washed with EtOAc (2×500 mL) to give a light yellow solid. The two batches were combined to afford the product (391.3 g). The filtrate was concentrated to a volume of 300 mL in vacuo and treated with hot (50° C.) MeOH (500 mL). The mixture was cooled to 5° C. in a refrigerator for 24 h. The resulting precipitate was collected by filtration and washed with EtOAc (2×200 mL) to afford an additional 44.3 g of product (total of 435.6 g, 95% yield).

Step 3: 2-chloro-1-(4-(4-chloro-3-methoxyphenyl) piperazin-1-yl)ethanone

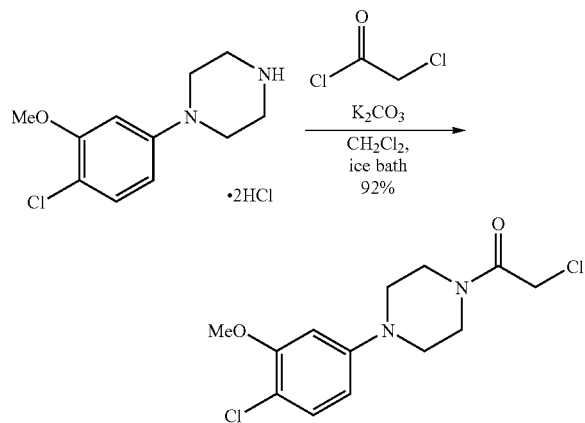

To a 3 L flask equipped with a mechanical stirrer was added 1-(4-chloro-3-methoxyphenyl)piperazine dihydrochloride (220 g, 0.73 mol, 1 equiv), $CH_2Cl_2$ (1000 mL), and water (1000 mL). The biphasic mixture was cooled to 5° C. with an ice-water bath. $K_2CO_3$ (506 g, 5 equiv) was added to the vigorously stirring solution in portions to minimize foaming. A solution of chloroacetyl chloride (124.4 g, 1.5 equiv) in $CH_2Cl_2$ (100 mL) was added dropwise from an addition funnel, while maintaining an internal temperature below 8° C. After 1 h, the cooling bath was removed, and the reaction warmed to room temperature. After an additional 1 h, the layers were partitioned. The aqueous phase was extracted with $CH_2Cl_2$ (2×300 mL), and the combined organic layers dried over 3:1 $Na_2SO_4/K_2CO_3$ (addition of $K_2CO_3$ helps the solution phase to become clear). After filtration, the filtrate was concentrated in vacuo, and the residue was dried for 16 h under vacuum to afford the product as an off-white solid (410 g, 92% yield).

Step 6: 7-azaindazole-3-carboxaldehyde

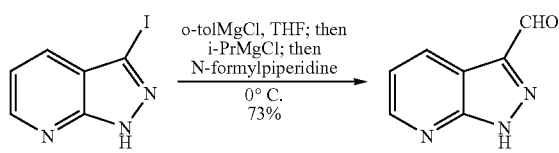

A 5 L 3-necked flask equipped with a digital thermometer, a 1 L addition funnel and mechanical stirrer (all glassware dried in oven and cooled in air for 30 min before use) was charged with 3-iodo-7-azaindaozle (196.0 g, 0.80 mol) and 1 L of anhydrous THF (in SureSeal bottle from Aldrich and used as is). The solids completely dissolved in THF at room temperature to form a dark brown solution. The flask was then cooled to −5° C. with an ice/NaCl bath and moderate stirring and o-tolylmagnesium chloride (1 M solution in THF, 880 mL, 1.1 equiv) was added dropwise to keep the internal temperature between −5° C. to −3° C. (after ~820 mL of o-tolyl-magnesium chloride solution was added, the temperature no longer rose). The whole addition process took 2 hr and 25 min. At the end of the addition, the mixture was a homogeneous dark brown solution.

After an additional 1 hr, isopropylmagnesium chloride solution (2 M in THF, 480 mL, 1.2 equiv) was added dropwise to keep internal temperature <4° C. After 25 min and about 200 mL isopropylmagnesium chloride solution was added, brown precipitate started to form. After a total of 380 mL of isopropylmagnesium chloride solution was added, the mixture became homogeneous again. The whole addition process was done in 45 min. After another 1 hr 25 min, a small amount of sample was taken out and quenched with $D_2O$. LCMS analysis of this sample indicated the complete Iodo-Mg exchange.

1-Formylpiperidine (120 mL, 1.3 equiv) was then added dropwise to keep the internal temperature between <2° C. After about 30 mL 1-formylpiperidine was added, the internal temperature did not go up anymore and rest of the 1-formylpiperidine was added relatively quickly. The whole addition process took 20 min. At the end of the addition, the mixture was still a dark homogeneous solution and was allowed to slowly warm up to room temperature and moderately stirred for 18 hr.

The mixture was re-cooled to 0° C. with an ice/NaCl bath and quenched by slow addition of a mixture of saturated $NH_4Cl$ solution (750 mL)/concentrated HCl solution (250 mL) to keep the internal temperature at <35° C. After the addition was complete, stirring was allowed to continue for 1 hr and a yellow precipitate appeared. The mixture was filtered and the solid was washed with THF (100 mL). The collected filtrate was transferred to a separation funnel and the pH of the aqueous layer was adjusted to between 5 and 6 with the addition of $NaHCO_3$ (around 5 g). The THF layer was separated and washed with sat. NaCl solution (2×100 mL). The combined aqueous layers (including the NaCl wash and quenched aqueous layer) was extracted with EtOAc (3×250 mL). The combined organic layers was dried ($Na_2SO_4$), filtered and evaporated in vacuo (bath temperature <30° C.) to give a brownish solid. This solid was triturated with $Et_2O$ (600 mL) and filtered. The collected solid was washed with $Et_2O$ (2×100 mL) to give 7-azaindazole-3-carboxaldehyde as a yellowish solid (86.6 g, 73%).

Step 4: 1-[4-(4-Chloro-5-ethoxy-2-fluorophenyl) piperazin-1-yl]-2-[3-formyl-pyrazolo[3,4-b]pyridin-1-yl]ethanone

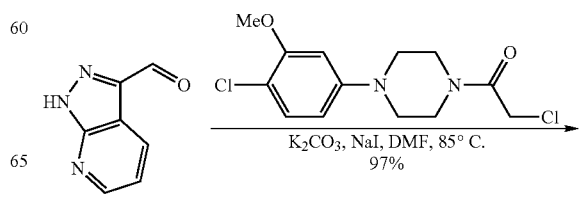

-continued

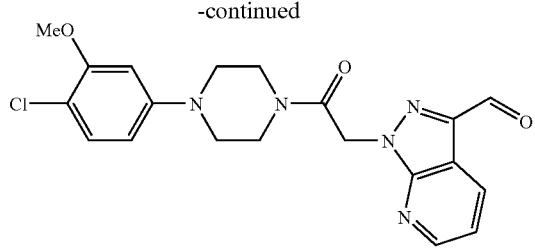

A mixture of 7-azaindazole-3-carboxaldehyde (86.6 g, 0.59 mol, 1 equiv), NaI (8.8 g, 0.1 equiv) and K$_2$CO$_3$ (162.5 g, 2 equiv) in DMF (0.5 L) in a 5 L flask was heated to 85° C. (the heating process took around 1.5 h). 2-chloro-1-(4-(4-chloro-3-methoxyphenyl)piperazin-1-yl)ethanone (175 g, 1 equiv) was added in small portions to the reaction mixture. The whole addition process took about 30 min. The mixture was then stirred at 85° C. for 30 min and LCMS confirmed that the reaction was complete. After cooling down to room temperature, the mixture was transferred to a 4 L flask with 2 L ice. The reaction flask was rinsed with small amount of acetone (30 mL) and transferred to the DMF/ice mixture in the 4 L flask also. A lot of brownish solids precipitated out. After the ice completely melted, the mixture was filtered. The collected solid was washed with water (1 L), blended, and then washed with water (1 L) to get rid of some residual DMF. The collected solid contained a lot of water, so it was dissolved in CH$_2$Cl$_2$ (4 L) and the mixture was transferred to a 5 L separation funnel. The bottom CH$_2$Cl$_2$ layer was separated and the top aq. layer was washed with CH$_2$Cl$_2$ (2×100 mL). The combined CH$_2$Cl$_2$ layers were dried (Na$_2$SO$_4$), filtered and evaporated in vacuo to give 1-[4-(4-Chloro-5-ethoxy-2-fluorophenyl)piperazin-1-yl]-2-[3-formyl-pyrazolo[3,4-b]pyridin-1-yl]ethanone as a brownish solid (236.4 g, 97%) which was used without purification.

Step 5: 1-[4-(4-Chloro-5-ethoxy-2-fluorophenyl)piperazin-1-yl]-2-[3-(1H-imidazol-2-yl)-pyrazolo[3,4-b]pyridin-1-yl]ethanone 1-[4-(4-Chloro-5-ethoxy-2-fluorophenyl)piperazin-1-yl]-2-[3-formyl-pyrazolo[3,4-b]pyridin-1-yl]ethanone (300 g, 723 mmol, 1 equiv), glyoxal trimer dihydrate (60.6 g, 0.4 equiv), and ammonium acetate (222.9 g, 4 equiv) were suspended in a mixture of THF (720 mL) and MeOH (720 mL) in a 5 L round-bottomed flask fitted with a magnetic stir bar and nitrogen inlet. Acetic acid (84 mL, 2 equiv) was added and the mixture was heated in a 45° C. oil bath (solids dissolved upon heating). After 12 hours, LC/MS analysis indicated complete consumption of aldehyde starting material and formation of desired product (LC/MS m/z (M+H)$^+$ 452.1). The MeOH/THF were removed by rotary evaporation. The residue was dissolved in 10% MeOH in CH$_2$Cl$_2$ (ca. 1.5 L) and the mixture was shaken vigorously with aqueous potassium carbonate (ca. 210 g potassium carbonate in ca. 1.5 L water, pH of aqueous=8-9). The layers were separated, and the aqueous layer was extracted with 10% MeOH in CH$_2$Cl$_2$ (2×100 mL). The combined organic layers were concentrated to give a brown oily solid. The crude product was suspended in 10% MeOH in EtOAc (ca. 1 L). Anhydrous Na$_2$SO$_4$ (ca. 60 g) and silica gel (ca. 100 g) were added and the slurry was heated gently with a heat gun to dissolve the crude product. The slurry was transferred to a 2 L fritted glass filter funnel containing silica gel (ca. 100 g, pre-equilibrated with 10% MeOH in EtOAc), and the product was eluted through the silica gel plug with 10% MeOH in EtOAc (ca. 6 L) and 1% Et$_3$N, 10% MeOH in EtOAc (ca. 10 L). (Note: Incomplete dissolution of the product and/or precipitation of product in the presence of silica gel complicated the filtration). The solvents were removed by rotary evaporation. The residue was triturated with MeCN (1×300 mL) and dried (rotary evaporation followed by high vacuum) to provide 1-[4-(4-chloro-5-ethoxy-2-fluorophenyl)piperazin-1-yl]-2-[3-(1H-imidazol-2-yl)-pyrazolo[3,4-b]pyridin-1-yl]ethanone as an off-white solid (190 g, 58%, LC/MS purity >98%).

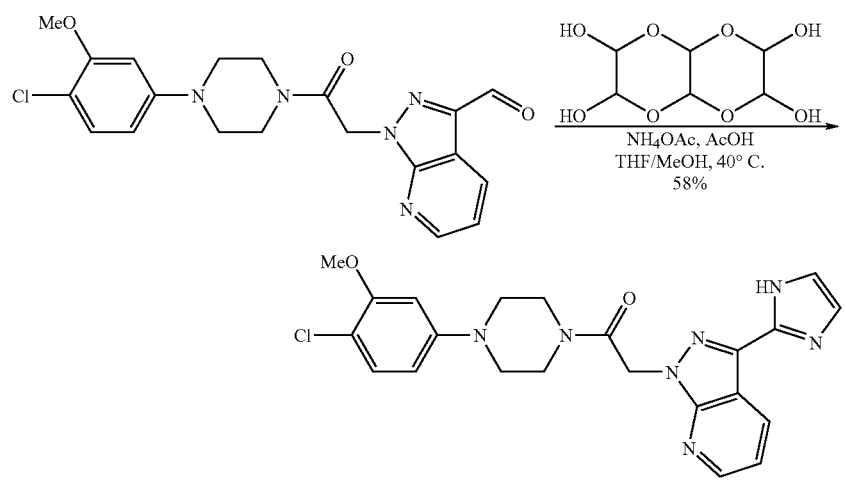

Step 7: 2-(3-1H-imidazol-2-yl)-1H-pyrazolo[3,4-b]pyridin-1-yl)-1-(4-(4-chloro-3-methoxyphenyl)piperazin-1-yl)ethanone hydrochloride salt

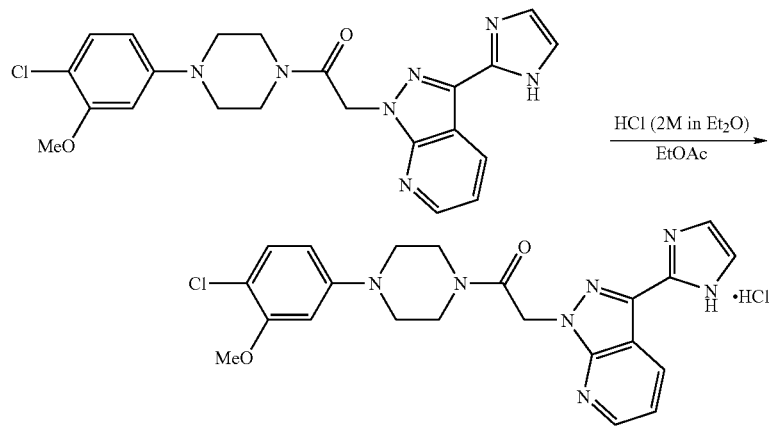

A 2 L flask with a magnetic stirrer was charged with the starting material (5.1 g, 11.28 mmol) and EtOAc (900 mL). The resulting suspension was heated to form a clear solution and cooled to room temperature under moderate stirring. HCl in Et$_2$O (2M, 6.2 mL, 12.42 mmol) was added dropwise to the resulting solution at room temperature over 5 min. After the addition, the resultant suspension was stirred at room temperature for another 1 h. The solid was collected by filtration and washed with Et$_2$O (150 mL×2) and dried in vacuo to afford 5.4 g of an off-white powder. A 250 mL flask with a magnetic stirrer was charged with the powder obtained above (5.4 g), acetone (100 mL) and deionized water (16 mL). The resulting suspension was heated to form a clear solution and stirred to cool. When the solution became cloudy (crystal seeds appeared), acetone (540 mL) was added slowly to the suspension over 20 min. The resulting suspension was heated to 50° C. and stirred for 2 h. Filtration while hot, washing with hot acetone (50 mL×2) and drying in vacuo gave 3.3 g (60%) of the product as an off-white solid: m.p. 164-165° C. The crystals appear as prisms under a polarizing microscope.

Example 19

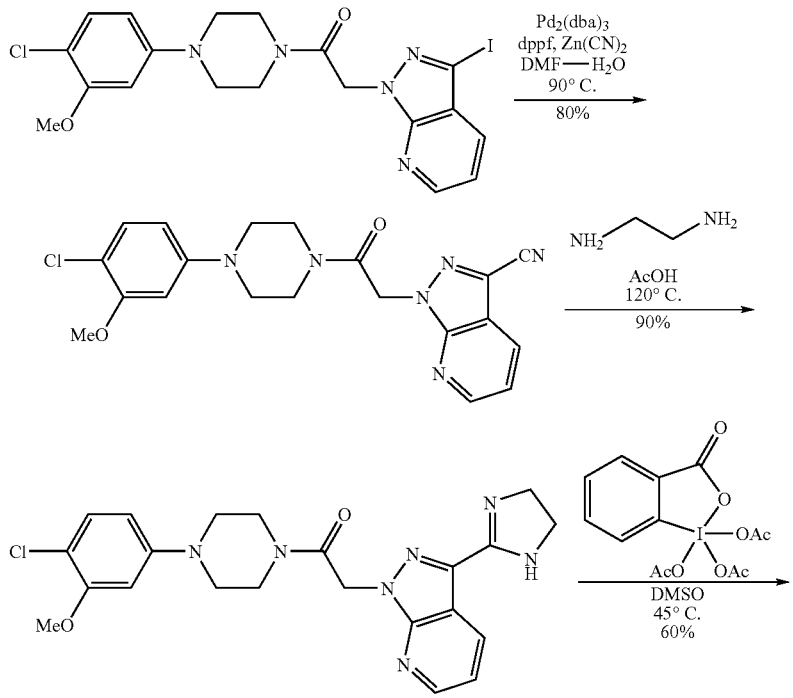

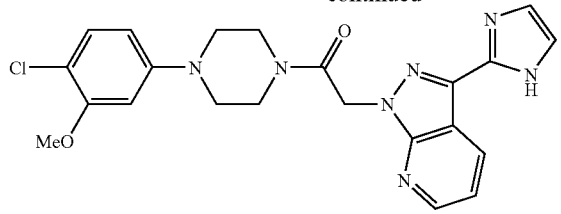

Step 1: Synthesis of 1-{2-[4-(4-Chloro-3-methoxy-phenyl)-piperazin-1-yl]-2-oxo-ethyl}-1H-pyrazolo[3,4-b]pyridine-3-carbonitrile

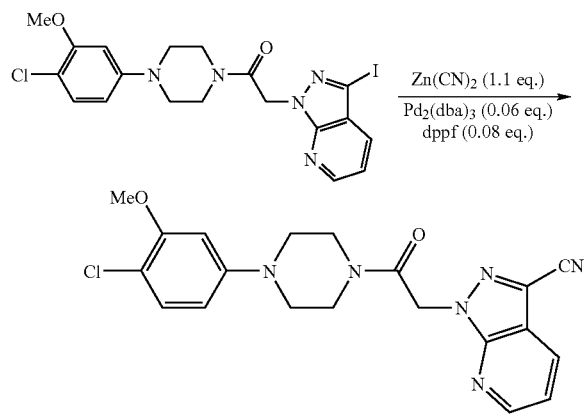

To a 2000 ml flask was charged with 1-[4-(4-Chloro-3-methoxy-phenyl)-piperazin-1-yl]-2-(3-iodo-pyrazolo[3,4-b]pyridin-1-yl)-ethanone (see U.S. application Ser. No. 11/474,132, published as U.S. 20070010524, 40 g, 78.1 mmol), dppf (3.86 g, 6.96 mmol), Zn(CN)$_2$ (9.6 g, 81.6 mmol), DMF (360 ml) and H$_2$O (20 ml). The resulting suspension was degassed using N$_2$ for 5 min, followed by addition of Pd$_2$(dba)$_3$ (4.24 g, 4.64 mmol). The reaction mixture was heated under N$_2$ at 90° C. for 2 h (monitor by TLC and LC-MS). After cooling to room temperature, diluted with EtOAc (1500 ml), filtered to remove the precipitate and washed with H$_2$O (1000×2 ml), saturated EDTA.4Na (800 ml×2), brine and dried over Na$_2$SO$_4$. After evaporation of the solvent, ether (150 mL) was added and stirred for 2 h. The resulting solid was filtered to give the desired product 30 g (93%) as light yellow powder. Recrystallization from refluxing CH$_3$CN (160 mL) afforded 26 g (80%) light yellow crystals: mp 183-185° C.; R$_t$=2.38 min; MS (ES) M+H expect 411.1, found 41.1.

Step 2: Synthesis of 1-(4-(4-chloro-3-methoxyphenyl)piperazin-1-yl)-2-(3-(4,5-dihydro-1H-imidazol-2-yl)-1H-pyrazolo[3,4-b]pyridin-1-yl)ethanone

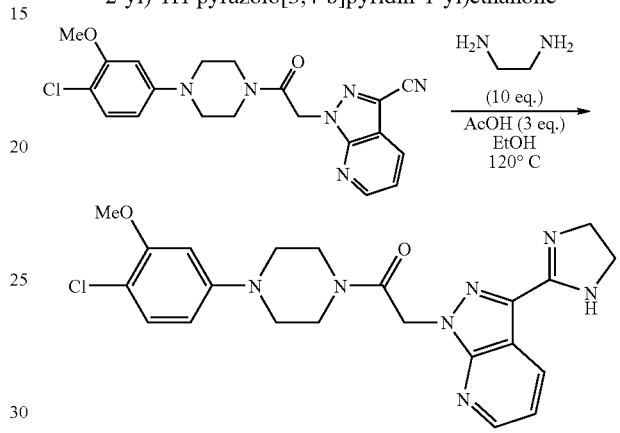

A 250 mL flask was charged with 1-(2-(4-chloro-3-methoxyphenyl)piperazin-1-yl)-2-oxoethyl)-1H-pyrazol[3,4-b]pyridine-3-carbonitrile (15.3 g, 37.2 mmol), EtOH (40 mL, ~1 M). Under ice-bath and stirring, AcOH (6.75 mL, 112 mmol) was added, followed by ethylenediamine (25 mL, 372 mmol). The resulting mixture was heated at 120° C. (bath) under N$_2$ (observed mixture starting refluxing) for 1.5 h. TLC and LC-MS indicated the disappearance of starting material and formation of imidazoline. After cooling to room temperature, mixture was diluted with DCM (700 mL) and washed with H$_2$O (350 mL). The H$_2$O layer was back extracted with DCM (150 mL), and the combined organic layer was washed brine (350 mL) and dried over MgSO$_4$. After evaporating of the solvent under reduced pressure, the residue was suspended in hot EtOAc (80 mL). After cooling to room temperature, the solid was collected by filtration and washed with EtOAc (30 mL) to afford the title compound as white powders (16 g, 95%) which was used directly for next step: mp 133-135° C.; R$_t$=1.369 min. MS (ES) M+H expect 454.2, found 454.4.

Step 3: 2-(3-1H-imidazol-2-yl)-1H-pyrazolo[3,4-b]pyridin-1-yl)-1-(4-(4-chloro-3-methoxyphenyl)piperazin-1-yl)ethanone

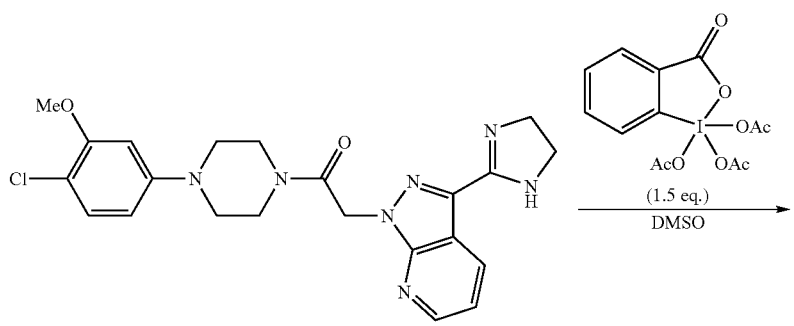

-continued

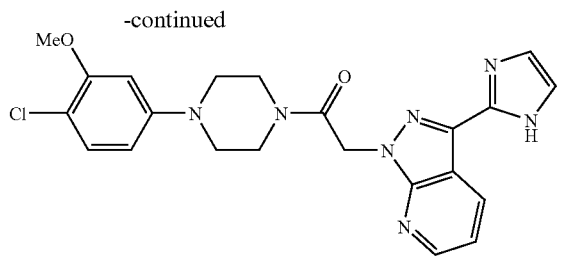

The above imidazoline (12.3 g, 27.1 mmol) in a 500 mL flask was charged with anhydrous DMSO (108 mL, ~0.25 M). DMP (17.2 g, 40.6 mmol) was added in portions under stirring. The resulting mixture was stirred at 45° C. under $N_2$ for 2 h (monitor by TLC and LC-MS). After cooling to room temperature, quenching the reaction with sat $Na_2S_2O_3$ (100 mL) (ice-bath), followed 3 N NaOH (100 mL) (pH 12 to 13) and $H_2O$ (300 mL) and extracted with DCM (600 mL+300 mL). The combined organic layer was washed with sat $NaHCO_3$ (300 mL), brine (300 mL) and dried ($MgSO_4$, 120 g). After evaporation of the organic solvent, the residue yellow solid (11 g) was dissolved in hot $CH_3CN$ (20 mL). After cooling to room temperature, the resulting solid was collected by filtration to afford 6.7 g (55%) of title compound as light tan crystals: mp 149-152° C.; $R_t$=1.309 min. MS (ES) M+H expect 452.2, found 452.4. Mother liquor was concentrated and afforded another 0.6 g (total isolated yield 60%).

Example 20

This example illustrates the evaluation of the biological activity associated with compounds of interest of the invention.

Materials and Methods
A. Cells
 1. CCR1 Expressing Cells
  a) THP-1 Cells

THP-1 cells were obtained from ATCC (TIB-202) and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% $CO_2$/95% air, 100% humidity at 37° C. and subcultured twice weekly at 1:5 (cells were cultured at a density range of $2\times10^5$ to $2\times10^6$ cells/mL) and harvested at $1\times10^6$ cells/mL. THP-1 cells express CCR1 and can be used in CCR1 binding and functional assays.

2. Chemotaxis Assays

Chemotaxis assays were performed using 5 μm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e., MIP-1α, CCL15/Leukotactin; R&D Systems; Minneapolis, Minn.) are use to evaluate compound mediated inhibition of CCR1 mediated migration. Other chemokines (i.e., SDF-1α; R&D Systems; Minneapolis, Minn.) are used as specificity controls. The lower chamber was loaded with 29 μl of chemokine (i.e., 0.1 nM CCL15/Leukotactin) and varying amounts of compound; the top chamber contained 100,000 THP-1 or monocyte cells in 20 μl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

B. Identification of Inhibitors of CCR1

One of the primary functions of chemokines is their ability to mediate the migration of chemokine receptor-expressing cells, such as white blood cells. To confirm that a compound of interest inhibited not only CCR1 specific binding and signaling (at least as determined by calcium mobilization assays), but also CCR1 mediated migration, a chemotaxis assay was employed. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were placed in the top compartment of a microwell migration chamber, while MIP-1α (or other potent CCR1 chemokine ligand) and increasing concentrations of a compound of interest was loaded in the lower chamber. In the absence of inhibitor, cells will migrate to the lower chamber in response to the chemokine agonist; if a compound inhibited CCR1 function, then the majority of cells will remain in the upper chamber. To ascertain a compound of interest's affinity for CCR1 as well as to confirm its ability to inhibit CCR1 mediated cell migration, inhibitory activity was titered over a $1\times10^{-10}$ to $1\times10^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate $IC_{50}$ values. $IC_{50}$ values are those compound concentrations required to inhibit the number of cells responding to a CCR1 agonist by 50%.

1. In Vivo Efficacy
  a) Rabbit Model of Destructive Joint Inflammation

A rabbit LPS study was conducted essentially as described in Podolin, et al. *J. Immunol.* 169(11):6435-6444 (2002). Female New Zealand rabbits (approximately 2 kilograms) were treated intra-articularly in both knees with LPS (10 ng). The compound of interest, for example 1.016, (formulated in 1% methocel) or vehicle (1% methocel) was dosed orally at a 5 ml/kg dose volume at two times (2 hours before the intra-articular LPS injection and 4 hours after the intra-articular LPS injection). Sixteen hours after the LPS injection, knees were lavaged and cells counts were performed. Beneficial effects of treatment were determined by reduction in the number of inflammatory cells recruited to the inflamed synovial fluid of the knee joints. Treatment with the compound of interest resulted in a significant reduction in recruited inflammatory cells.

b) Evaluation of a Compound of Interest in a Rat Model of Collagen Induced Arthritis A 17 day developing type II collagen arthritis study is conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter are taken, and reduced joint swelling is taken as a measure of efficacy.

In Table 2 (below), structures and activity are provided for representative compounds described herein. Activity is provided as follows for the chemotaxis assay as described above: +, $IC_{50}$>100 nM; ++, $IC_{50}$≦100 nM.

TABLE 2

| Structure |
|---|
| 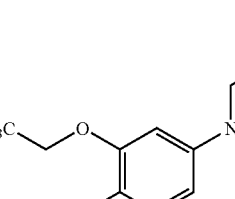 1.001/++ |
| 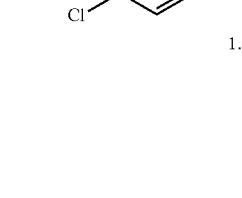 1.002/++ |

TABLE 2-continued

| Structure |
|---|
| 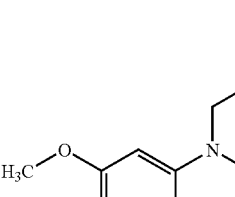 1.003/++ |
| 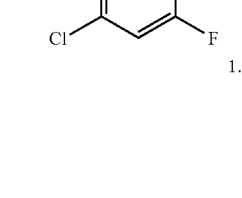 1.004/++ |
| 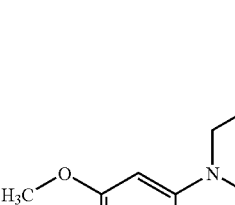 1.005/++ |
| 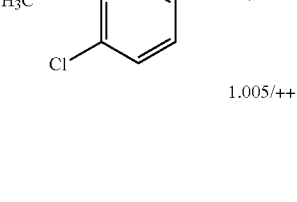 1.006/++ |

TABLE 2-continued
Structure
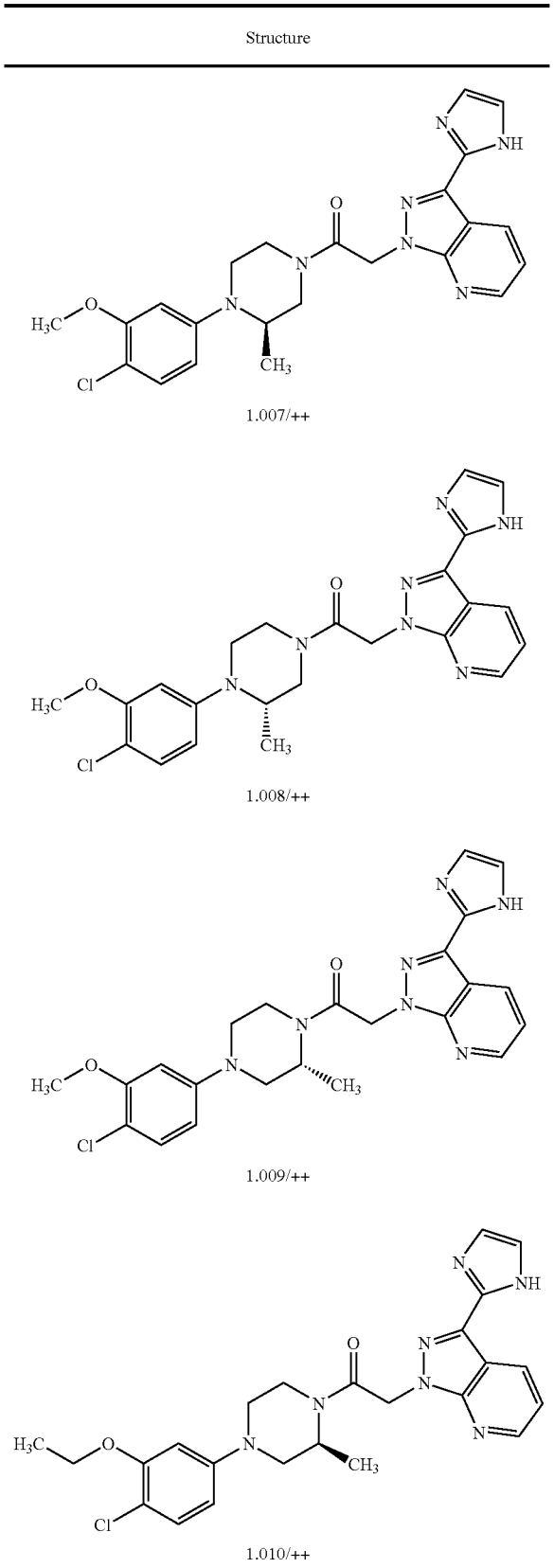
1.007/++
1.008/++
1.009/++
1.010/++
TABLE 2-continued
Structure
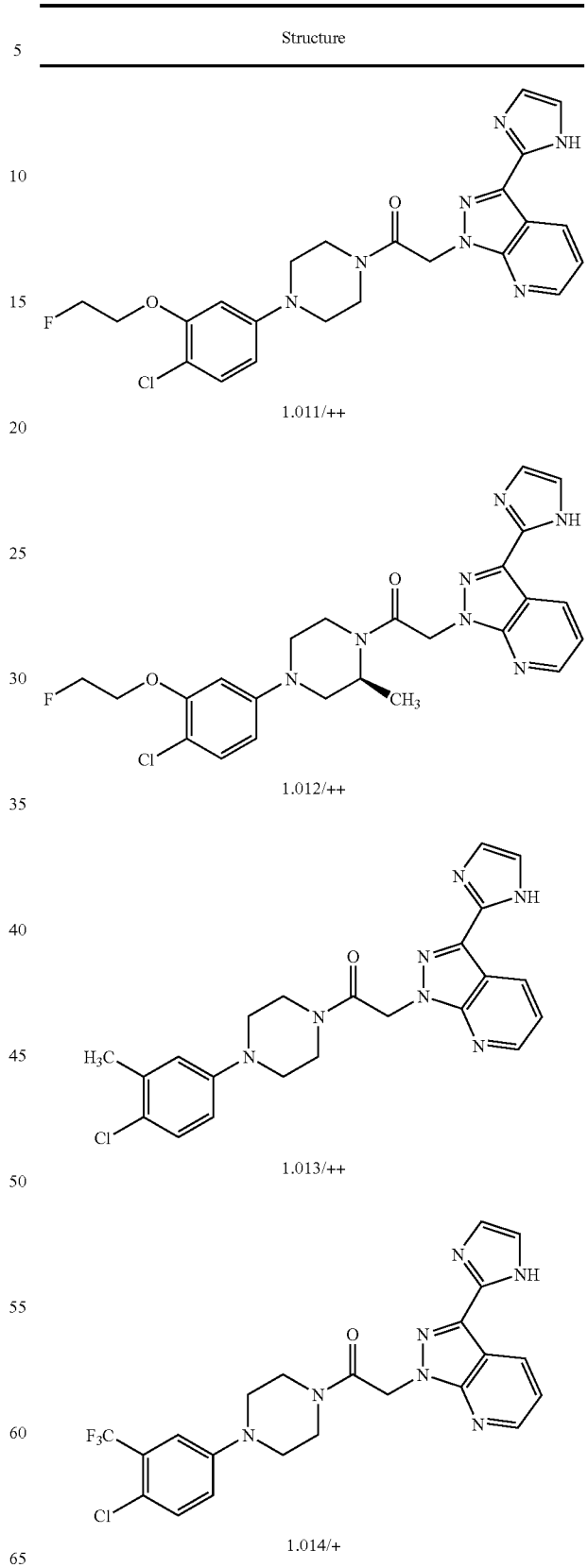
1.011/++
1.012/++
1.013/++
1.014/+

TABLE 2-continued

Structure

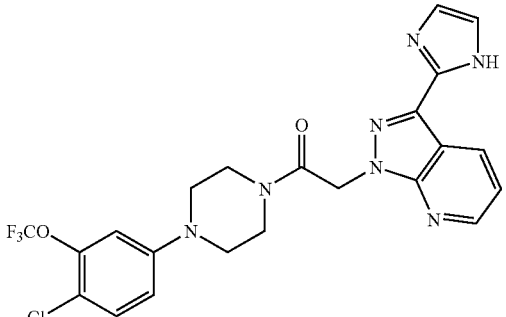

1.015/+

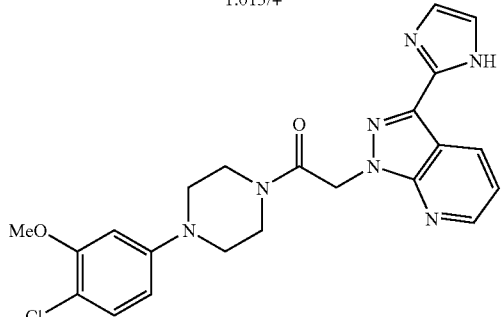

1.016/++

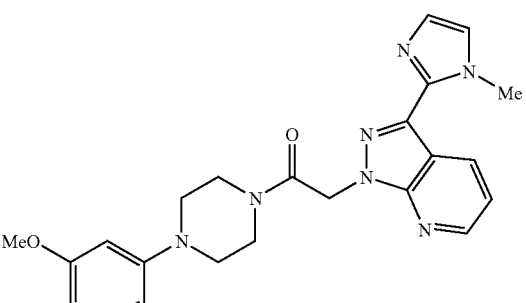

1.017/++

What is claimed is:

1. A compound having the formula:

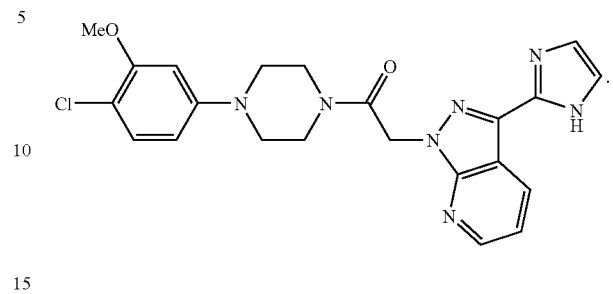

2. A compound having the formula:

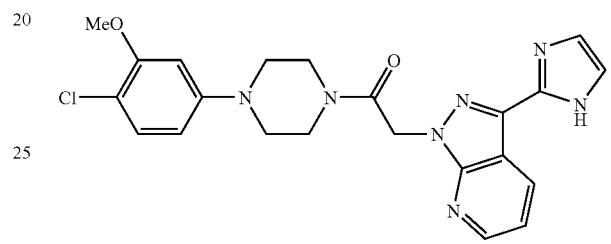

or a pharmaceutically acceptable salt, hydrate or N-oxide thereof.

3. A compound of claim 2, in a hydrate form.

4. A compound of claim 2, in a pharmaceutically acceptable salt form.

5. A pharmaceutical composition comprising the compound of claim 1 and a pharmaceutically acceptable excipient or carrier.

6. A pharmaceutical composition comprising the compound of claim 2 and a pharmaceutically acceptable excipient or carrier.

* * * * *